United States Patent [19]

Kindon et al.

[11] Patent Number: 6,162,808

[45] Date of Patent: Dec. 19, 2000

[54] COMPOUNDS

[75] Inventors: Nicholas Kindon; Premji Meghani; Stephen Thom, all of Loughborough, United Kingdom

[73] Assignee: AstraZeneca U.K. Limited, London, United Kingdom

[21] Appl. No.: 09/091,187

[22] PCT Filed: May 18, 1998

[86] PCT No.: PCT/SE98/00940

§ 371 Date: Jun. 10, 1998

§ 102(e) Date: Jun. 10, 1998

[87] PCT Pub. No.: WO98/54180

PCT Pub. Date: Dec. 3, 1998

[30] Foreign Application Priority Data

May 28, 1997 [SE] Sweden .................................. 9702002

[51] Int. Cl.[7] ..................... A61K 31/505; C07D 239/02; C07D 403/00

[52] U.S. Cl. .......................... 514/269; 514/274; 544/298; 544/301

[58] Field of Search ...................................... 514/269, 274; 544/298, 301

[56] References Cited

FOREIGN PATENT DOCUMENTS

92/13844   8/1992   WIPO .

OTHER PUBLICATIONS

J.Org.Chem.35/5,587–591(1974);C.W.Whitehead et al. Reacn.of Pyrimidines with Diaryl Cats, Mar. 1974.

J. Org. Chem.35/5,591–595(1974),C.W. Whitehead et al. 37 Reacn. of Diaryl Cats. W/Amino–pyrimids. Mar. 1974.

Primary Examiner—Mukund J. Shah
Assistant Examiner—Sudhaker B. Patel
Attorney, Agent, or Firm—Nixon & Vanderhye

[57] ABSTRACT

The invention relates to new pharmaceutically active compounds which are P2-purinoceptor 7-transmembrane (TM) G-protein coupled receptor antagonists, compositions containing them and processes for their preparation.

10 Claims, No Drawings

COMPOUNDS

The invention provides new pharmaceutically active compounds, compositions containing them and processes for their preparation. The compounds are useful in therapy because they are P2-purinoceptor 7-transmembrane (TM) G-protein coupled receptor antagonists.

ATP receptors have been shown to be present on a wide number of different cell types (Dubyak et al Am J Physiol (1993) 265, C577–C606). Neutrophils, monocytes and macrophages have been isolated from several species including humans and ATP and/or UTP have been shown to increase intracellular calcium levels. Activation of these receptors on leukocytes can either directly stimulate certain types of inflammatory response or can prime the effector cells to other inflammatory mediators in vivo. ATP can upregulate the expression of adhesion molecules (Freyer et al J Immun. (1988) 141, 580–586) which causes enhanced adhesion of circulating leukocytes to endothelial cells and their enhanced migration into the tissue space. ATP has also been shown to promote chemotaxis of both neutrophils and eosinophils (Verghese et al J. B. C. (1996) 271, 15597–15601 and Burders et al Blood (1993) 81, 49–55) which may promote an inflammatory response. ATP priming of neutrophils can also potentiate superoxide production (Seifert et al Eur J Biochem (1989) 181, 277–285). ATP receptors are also present on a number of other cell types such as chondrocytes, keratinocytes, microglia and goblet cells (Leong et al BBA (1994) 1201, 298–304; Pillai et al J Clin Invest (1992) 90, 42–51; Walz et al J Neuroscience (1993) 13, 4403–4411 and Abdullah et al Biochem J (1996) 316, 943–951). Stimulation of the receptors on these cells can stimulate or enhance inflammatory responses and antagonist of the receptor may therefore be of use in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. ATP receptors have also been reported on tumour cells (Dubyak et al J. Biol. Chem., (1985) 260, 10653–10661 and Wagner et al Gastroenterolgy, (1997), 112(4) suppl. page A1198) and may be involved in the development of cancer. Antagonists may therefore be useful in treatment of cancer.

According to the invention there is provided a compound of formula (I) or salts thereof:

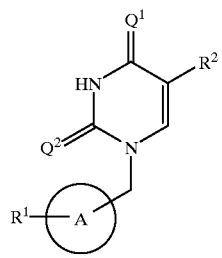

(I)

in which:
A is a 5-membered heterocyclic ring containing 1 to 3 heteroatoms selected from nitrogen, oxygen or sulfur;
$R^1$ is $(CH_2)_nCO_2H$ where n is 1 or 2, $(CH_2)_q$tetrazol-5-yl where q is 0, 1 or 2 or $R^1$ is $COR^3$ where $R^3$ is amino, alkylamino, dialkyl amino, NHOalkyl, $NHSO_2$alkyl, OH, $N(CH_2CO_2H)_2$ or a group of formula (i):

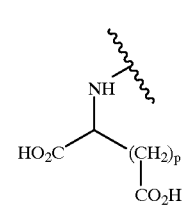

(i)

in which p is 1 or 2, or $R^3$ is a group of formula (ii):

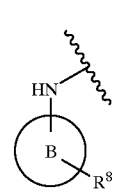

(ii)

where B is a 5-membered heterocyclic ring containing 1 to 4 heteroatoms selected from nitrogen, oxygen or sulfur and $R^8$ is hydrogen or a group $CH_2CO_2H$, $CH_2CON(CH_2CO_2H)_2$ or $CH_2COR^9$ where $R^9$ is a group of formula (i) as defined above or a group of formula (iii):

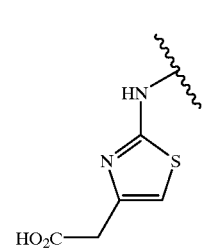

(iii)

$R^2$ is a group of formula (iv) or (v):

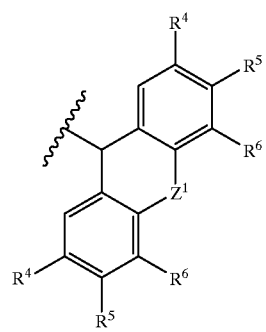

(iv)

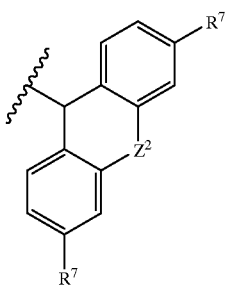

(v)

where R⁴ groups are independently hydrogen, halogen, methoxy, methylthio or $C_{1-2}$alkyl (optionally substituted by one or more fluorine atoms);
R⁵ groups are independently hydrogen, halogen, hydroxy, $C_{1-3}$ alkylthio, $C_{1-4}$alkyl (optionally substituted by one or more fluorine atoms), $C_{3-4}$cycloalkyl, $MeOCH_2$, $MeSCH_2$ or $C_{1-2}$alkoxy;
R⁶ groups are independently hydrogen, halogen or methyl (optionally substituted by one or more fluorine atoms);
$Z^1$ is CH=CH, CF=CH or CF=CF;
$Z^2$ is is a single bond, oxygen, sulphur, $CH_2CH=CH$, $CH_2CH=CHCH_2$ or a $C_{1-4}$alkylene group optionally interrupted by an oxygen or sulphur atom;
R⁷ is hydrogen, halogen, $C_{1-2}$alkyl, $CF_3$ or a methylthio group;
$Q^1$ and $Q^2$ each independently represent an O or S; provided that when $Q^1$ is oxygen, $R^2$ is a group of formula (iv).

Alkyl groups, whether alone or as part of another group, can be straight chain or branched.

Unless stated otherwise the term alkyl means $C_{1-6}$alkyl such as methyl, ethyl, propyl, butyl etc.

Suitably A is a 5-membered heterocyclic ring containing 1 to 3 heteroatoms selected from nitrogen, oxygen or sulfur. Preferred rings A include thiazole, oxazole, furan and thiophene.

Suitably $R^1$ is $(CH_2)_nCO_2H$ where n is 1 or 2, $(CH_2)_q$tetrazol-5-yl where q is 0, 1 or 2 or $R^1$ is $COR^3$ where $R^3$ is amino, alkylamino, dialkylamino, NHOalkyl, $NHSO_2$alkyl, OH, $N(CH_2CO_2H)_2$ or a group of formula (i) or (ii).

Preferably $R^1$ is a group $COR^3$. Preferably $R^3$ is OH or $NHSO_2Me$ or $R^3$ is a group of formula (i), in particular a group of formula (i) where p is 1, $R^3$ is a group of formula (ii) where B is a thiazole and $R^8$ is a group $CH_2CO_2H$ or $CH_2COR^9$ where $R^9$ is a group of formula (i) or $R^3$ is a group of formula (ii) where B is a tetrazole ring and $R^8$ is hydrogen.

Suitably $R^2$ is a group of formula (iv) or (v). Preferably $R^2$ is a group of formula (iv) where $Z^1$ is CH=CH.

Suitably R⁴ groups are independently hydrogen, halogen, methoxy, methylthio or $C_{1-2}$alkyl (optionally substituted by one or more fluorine atoms). Preferably both $R^4$ groups are hydrogen or one is hydrogen and the other is $C_{1-2}$alkyl or methoxy.

Suitably R⁵ groups are independently hydrogen, halogen, hydroxy, $C_{1-3}$ alkylthio or $C_{1-4}$alkyl (optionally substituted by one or more fluorine atoms), $C_{3-4}$ cycloalkyl, $MeOCH_2$, $MeSCH_2$ or $C_{1-2}$alkoxy. Preferably both R⁵ groups are hydrogen, one R⁵ group is hydrogen or hydroxy and the other is $C_{1-4}$alkyl (most preferably methyl or ethyl), or both R⁵ groups are $C_{1-4}$alkyl (most preferably methyl or ethyl, more preferably both methyl), or both $R^5$ groups are $CF_3$ or halogen in particular bromo or chloro.

Suitably R⁶ groups are independently hydrogen, halogen or methyl (optionally substituted by one or more fluorine atoms). Preferably both R⁶ groups are hydrogen or methyl. More preferably both R⁶ groups are hydrogen or one is hydrogen and the other is methyl.

Suitably $Q^1$ and $Q^2$ each independently represent an O or S. Preferably $Q^1$ is S and $Q^2$ is O or S.

Particularly preferred compounds of the invention include:

2-[[5-{5H-Dibenzo[a,d]cyclohepten-5-yl}-3,4-dihydro-2-oxo-4-thioxo-1(2H)-pyrimidinyl]methyl]-4-thiazolecarboxylic acid, 2-[[5-{5H-Dibenzo[a,d]cyclohepten-5-yl}-3,4-dihydro-2-oxo-4-thioxo-1(2H)-pyrimidinyl]methyl]-5-thiazolecarboxylic acid, 2-[[5-{5H-Dibenzo[a,d]cyclohepten-5-yl}-3,4-dihydro-2-oxo-4-thioxo-1(2H)-pyrimidinyl]methyl]-4-oxazolecarboxylic acid, 5-[[5-{5H-Dibenzo[a,d]cyclohepten-5-yl}-3,4-dihydro2-oxo4-thioxo-1(2H)-pyrimidinyl]methyl]-2-furancarboxylic acid, 5-[5H-Dibenzo[a,d]cyclohepten-5-yl]-3,4-dihydro-1-[4-[1H-tetrazol-5-yl]thiazol-2-ylmethyl]-4-thioxo-2(1H)-pyrimidinone, 4-[[5-{5H-Dibenzo[a,d]cyclohepten-5-yl}-3,4-dihydro-2-oxo-4-thioxo-1(2H)-pyrimidinyl]methyl]-2-thiophenecarboxylic acid, 2-[[5-{5H-Dibenzo[a,d]cyclohepten-5-yl}-3,4-dihydro-2-oxo-4-thioxo-1(2H)-pyrimidinyl]methyl]-4-thiazoleacetic acid, 2-[[5-{2,8-Dimethyl-5H-dibenzo[a,d]cyclohepten-5-yl}-3,4-dihydro-2-oxo-4-thioxo-1(2H)-pyrimidinyl]methyl]-4-thiazolecarboxylic acid, N-[2-[[5-{2,8-Dimethyl-5H-dibenzo[a,d]cyclohepten-5-yl}-3,4-dihydro-2-oxo4-thioxo-1(2H)-pyrimidinyl]methyl]thiazol4-ylcarbonyl]-L-aspartic acid, 2-[[2-[[5-{2,8-Dimethyl-5H-dibenzo[a,d]cyclohepten-5-yl}-3,4-dihydro-2-oxo4-thioxo-1(2H)-pyrimidinyl]methyl]thiazol-4-ylcarbonyl]amino]-4-thiazoleacetic acid, 5-[[5-{2,8-Dimethyl-5H-dibenzo[a,d]cyclohepten-5-yl}-3,4-dihydro-2-oxo-4-thioxo-1(2H)-pyrimidinyl]methyl]-2-furancarboxylic acid, 5-[[5-{2,8-Dimethyl-5H-dibenzo[a,d]cyclohepten-5-yl}-3,4-dihydro-2,4-dioxo-1(2H)-pyrimidinyl]methyl]-2-furancarboxylic acid, 2-[[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonyl]amino]-4-thiazoleacetic acid, 2-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-ylkcetylaminol-4-thiazoleacetic acid, N-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol4-yl]acetyl]-L-aspartic acid, N-Carboxymethyl-N-[[2-[5-[[5-{2,8-dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]glycine, 2-[[5-{2,8-Dibromo-5H-dibenzo[a,d]cyclohepten-5-yl}-3,4-dihydro-2-oxo-4-thioxo-1(2H)-pyrimidinyl]methyl]-4-thiazolecarboxylic acid, (±)-5-[[3,4-Dihydro-5-{2,3,8-trimethyl-5H-dibenzo[a,d]
  cyclohepten-5-yl}-2-oxo-4-thioxo-1(2H)-pyrimidinyl]
  methyl]-2-furancarboxylic acid,
2-[[5-{2,8-Diethyl-5H-dibenzo[a,d]cyclohepten-5-yl}-3,4-
  dihydro-2-oxo-4-thioxo-1(2H)-pyrimidinyl]methyl]-4-
  thiazolecarboxylic acid,
(±)-2-[[3,4-Dihydro-5-{2-methoxymethyl-8-methyl-5H-
  dibenzo[a,d]cyclohepten-5-yl}-2-oxo-4-thioxo-1(2H)-
  pyrimidinyl]methyl]-4-thiazolecarboxylic acid,
(±)-5-[[3,4-Dihydro-5-{3-methoxy-2,8-dimethyl-5H-
  dibenzo[a,d]cyclohepten-5-yl}-2,4-1(2H)-pyrimidinyl]
  methyl]-2-furancarboxylic acid,
5-[[5-{2,8-Bis(trifluoromethyl)-5H-dibenzo[a,d]
  cyclohepten-5-yl}-3,4-dihydro-2-oxo4-thioxo-1(2H)-
  pyrimidinyl]methyl]-2-furancarboxylic acid,
5-[[5-{2,8-Bis(trifluoromethyl)-5H-dibenzo[a,d]
  cyclohepten-5-yl}-3,4-dihydro-2,4-dioxo-1(2H)-
  pyrimidinyl]methyl]-2-furancarboxylic acid,
(±)-5-[[5-{2-Ethyl-8-methyl-5H-dibenzo[a,d]cyclohepten-
  5-yl}-3,4-dihydro-2,4-dioxo-1(2H)-pyrimidinyl]methyl]-
  2-furancarboxylic acid,
(±)-5-[[5-{2-Ethyl-5H-dibenzo[a,d]cyclohepten-5-yl}-3,4-
  dihydro-2,4-dioxo-1(2H)-pyrimidinyl]methyl]-2-
  furancarboxylic acid,
N-[5-[[5-{2,8-Dimethyl-5H-dibenzo[a,d]cyclohepten-5-
  yl}-3,4-dihydro-2-oxo4-thioxo-1(2H)-pyrimidinyl]
  methyl]furan-2-ylcarbonyl]-L-aspartic acid,
2-[[5-{10,11-Dihydro-5H-dibenzo[a,d]cyclohepten-5-yl}-3,
  4-dihydro-2-oxo-4-thioxo-1(2H)-pyrimidinyl]methyl]-4-
  thiazolecarboxylic acid,
(±)-5-[[3,4-Dihydro-5-{2-methyl-8-[1-methylethyl]-5H-
  dibenzo[a,d]cyclohepten-5-yl}-2,4-dioxo-1(2H)-
  pyrimidinyl]methyl]-2-furancarboxylic acid,
5-[[5-{2,8-Dichloro-5H-dibenzo[a,d]cyclohepten-5-yl}-3,
  4-dihydro-2-oxo-4-thioxo-1(2H)-pyrimidinyl]methyl]-2-
  furancarboxylic acid,
(±)-5-[[5-{2-Ethyl-8-methyl-5H-dibenzo[a,d]cyclohepten-
  5-yl}-3,4-dihydro-2-oxo-4-thioxo-1(2H)-pyrimidinyl]
  methyl]-2-furancarboxylic acid,
(±)-2-[[5-[[5-{2-Ethyl-8-methyl-5H-dibenzo[a,d]
  cyclohepten-5-yl}-3,4-dihydro-2-oxo-4-thioxo-1(2H)-
  pyrimidinyl]methyl]furan-2-ylcarbonyl]amino]4-
  thiazoleacetic acid,
5-[[5-{2,8-Dimethyl-5H-dibenzo[a,d]cyclohepten-5-yl}-3,
  4-dihydro-2-oxo-4-thioxo-1(2H)-pyrimidinyl]methyl]-N-
  [1H-tetrazol-5-yl]-2-furancarboxamide,
(±)-5-[[3,4-Dihydro-5-{2-methyl-8-propyl-5H-dibenzo[a,d]
  cyclohepten-5-yl}-2-oxo-4-thioxo-1(2H)-pyrimidinyl]
  methyl]-2-furancarboxylic acid,
(±)-2-[[5-[[3,4-Dihydro-5-{2-methyl-8-propyl-5H-dibenzo
  [a,d]cyclohepten-5-yl}-2-oxo-4-thioxo-1(2H)-
  pyrimidinyl]methyl]furan-2-yl]carbonyl]amino]-4-
  thiazoleacetic acid,
5-[[5-{2-ethyl-8-methyl-5H-dibenzo[a,d]cyclohepten-5-
  yl}-3,4-dihydro-2-oxo-4-thioxo-1(2H)-pyrimidinyl]
  methyl]-N-[1H-tetrazol-5-yl]-2-furancarboxamide,
2-[[5-{2,8-Dimethyl-5H-dibenzo[a,d]cyclohepten-5-yl}-3,
  4-dihydro-2-oxo-4-thioxo-1(2H)-pyrimidinyl]methyl]-4-
  oxazolecarboxylic acid,
2-[[5-{2,8-Dimethyl-5H-dibenzo[a,d]cyclohepten-5-yl}-3,
  4-dihydro-2-oxo-4-thioxo-1(2H)-pyrimidinyl]methyl]-N-
  methylsulphonyl-4-oxazolecarboxamide,
2-[[5-{2,8-Dimethyl-5H-dibenzo[a,d]cyclohepten-5-yl}-3,
  4-dihydro-2-oxo-4-thioxo-1(2H)-pyrimidinyl]methyl]-N-
  methyl-4-oxazolecarboxamide,
and pharmaceutically acceptable salts thereof.

In a further aspect the invention provides a process for the preparation of a compound of formula (I) which comprises reacting a compound of formula (II):

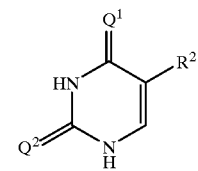

(II)

where $Q^1$, $Q^2$ and $R^2$ are as defined in formula (I) or are protected derivatives thereof with a compound of formula (III):

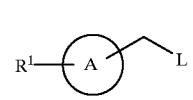

(III)

where $R^1$ and A are as defined in formula (I) or are protected derivatives thereof and L is a leaving group, and optionally thereafter in any order:
  removing any protecting groups
  converting the compound of formula (I) into a further compound of formula (I)
  forming a salt Reaction of compounds of formulae (II) and (II) can be carried out in the presence of a suitable base, for example a metal carbonate such as potassium carbonate or cesium carbonate in a suitable polar solvent such as dimethylformamide or dimethylsulphoxide at 10° C. to 80° C. Preferably L is halogen, in particular bromo. Alternatively the compound of formula (II) can be silylated with a suitable silylating reagent such as a trialkylsilylchloride and/or 1,1,1,3,3,3-hexamethyldisilazane in a suitable solvent such as pyridine, toluene or 1,4-dioxane at a temperature of about 80° C. to about 140° C. followed by addition of the compound of formula (III) in a suitable solvent such as acetonitrile at elevated temperature, for example at reflux. We prefer to silylate using bis(trimethylsilyl) trifluoroacetamide in refluxing 1,2-dichloroethane followed by treatment with the appropriate compound of formula (III) (where L is halogen, preferably bromide or chloride) in acetonitrile and 1,2-dichloroethane at reflux.

It will be appreciated by those skilled in the art that in the process described above the functional groups of intermediate compounds may need to be protected by protecting groups.

Functional groups of which it is desirable to protect include hydroxy, amino and carboxylic acid. Suitable protecting groups for hydroxy include organosilyl groups (e.g. tert-butyldimethylsilyl tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

In particular compounds of formula (III) where $R^1$ contains a carboxylic acid group can be protected as esters, particularly as $C_{1-6}$alkyl esters. Basic hydrolysis of such esters can be performed using metal hydroxides or quaternary ammonium hydroxides such as sodium hydroxide in a solvent such as an aqueous alcohol, 1,4-dioxane, tetrahydrofuran or dimethylformamide at a temperature between 10° C. and 100° C. Where $Q^1/Q^2$ are oxygen, acidic hydrolysis may also be performed using mineral acid such as HCl or a strong organic acid such as trifluoroacetic acid in a suitable solvent such as 1,4-dioxane. We prefer basic hydrolysis using lithium hydroxide in aqueous tetrahydrofuran or aqueous methanol at ambient temperature.

Compounds of formula (I) where $R^1$ is $COR^3$ and $R^3$ is a group of formula (i) or (ii) can be prepared by reacting a compound of formula (I) where $R^1$ is $CO_2H$ with the amine corresponding to formulae (i) and (ii) using standard methods employed in peptide synthesis, e.g. the use of a coupling reagent. Coupling agents which may be used include 1,1'-carbonyldiimidazole and 1,3-dicyclohexylcarbodiimide in a suitable solvent such as dimethylformamide, dichloromethane, tetrahydrofuran or acetonitrile at about 0° C. to about 30° C. We prefer to use bromo-tris(pyrrolidino)-phosphonium hexafluorophosphate with a trialkylamine such as N,N-diisopropylethylaamine and 4-dimethylaminopyridine in dimethylformamide at ambient temperature.

Compounds of formula (I) where $Q^1$ is oxygen can be converted to a corresponding compound of formula (I) where $Q^1$ is sulphur using standard thiation conditions for conversion of uridine and thymidine nucleosides into their corresponding thio-nucleoside derivatives (see "Chemistry of Nucleosides and Nucleotides" edited by Leroy B. Townsend, Plenum Press volume 1). Thiation may be achieved using reagents such as diphosphorus pentasulphide or Lawesson's reagent in a solvent such as pyridine, 1,4-dioxane, toluene, xylene, or tetrahydrofuran at a temperature of about 50° C. to about 130° C. We prefer to use Lawesson's reagent in 1,4-dioxane at about 100° C.

Compounds of formula (II) where $Q^1$ and $Q^2$ are oxygen can be prepared by reaction of a compound of formula (IV):

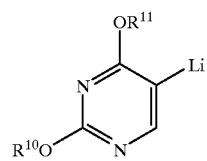

(IV)

where $R^{10}$ and $R^{11}$ are independently $C_{1-6}$alkyl or benzyl with a compound of formula (V) or (VI):

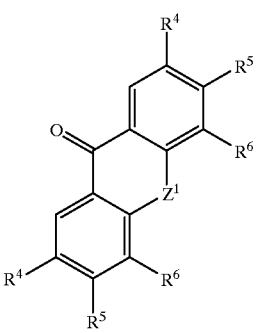

(V)

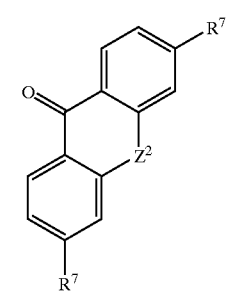

(VI)

where $Z^1$, $Z^2$, $R^4$, $R^5$, $R^6$ and $R^7$ are as defined in formula (I) followed by reduction of the resulting alcohol. Compounds of formula (IV) are prepared by treating the corresponding halide with an alkyl lithium reagent (alkyl=n-Butyl, sec-Butyl, tert-Butyl) in solvents such as tetrahydrofuran or diethyl ether at low temperature e.g. −40° C. to −78° C.

The resulting alcohol can then be reduced and deprotected to compounds of type (II) by treatment with a trialkylsilane such as triethylsilane in a suitable solvent such as dichloromethane, chloroform, or 1,2-dichloroethane and an acid or Lewis acid such as trifluoroacetic acid or borontrifluoride diethyl ether complex. We preferred to perform the metal halogen exchange on 5-bromo-2,4-bis(1,1-dimethylethoxy)pyrimidine using n-butyllithium at about −78° C. in tetrahydrofuran.

When the lithio species is quenched with a substituted 10,11-dihydro-5H-dibenzo[a,d]cyclohepten-5-one the resulting substituted 10,11-dihydro-5-{2,4-bis(alkoxy)pyrimidin-5-yl)-5H-dibenzo[a,d]cyclohepten-5-ol can then be converted to the uracil (II) (where $Z^1$ is CH=CH) by refluxing in a carboxylic acid solvent (Chem. Ber., 1989, 122, 1595). We prefer to use acetic acid. In some cases further treatment with trifluoroacetic acid at reflux may be required for the dehydration to give the substituted uracil (II).

Compounds of formula (II) can also be prepared from uracil and the appropriately substituted 5H-dibenzo[a,d]cyclohepten-5-ol by refluxing in a carboxylic acid solvent such as acetic acid (J.Org.Chem., 1974, 39, 587).

Compounds of formula (III) can be prepared from compounds of formula (VII):

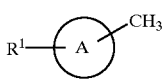

(VII)

where R¹ and A are as defined in formula (I) by treating with, for example, a halogenating agent. Suitable reagents include N-bromosuccinamide in a suitable solvent such as chloroform at elevated temperature and irradiated with strong light. Preferably the reaction is carried out in the presence of a catalytic amount of benzoyl peroxide at reflux and irradiated with a 500 W halogen lamp.

Compounds of formula (I) in which $Q^1$ and $Q^2$ are both oxygen can also be prepared from thioarnides of formula (VIII):

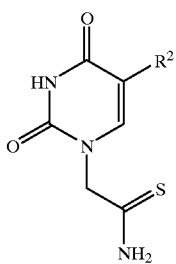

(VIII)

where $R^2$ is as defined in formula (I) with the appropriate alpha haloketone heated under reflux in an appropriate solvent such as ethanol.

Compounds of formula (VIII) can be prepared from the corresponding nitrile of formula (IX):

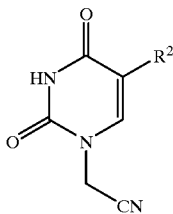

(IX)

where $R^2$ is as defined in formula (I) by treatment with $H_2S$ in the presence of a trialkylamine, preferably triethylamine, and pyridine. Compounds of formula (IX) can be prepared from a uracil of formula (II) and bromoacetonitrile using the silylation procedures described above.

Salts of the compounds of formula (I) may be formed by reacting the free acid, or a salt thereof, with one or more equivalents of the appropriate base (for example ammonium hydroxide optionally substitued by $C_{1-6}$-alkyl or an alkali metal or alkaline earth metal hydroxide). The reaction may be carried out in a solvent or medium in which the salt is insoluble or in a solvent in which the salt is soluble, e.g. water, alcohol or acetone, which may be removed in vacuo, or by freeze drying. The reaction may also be a metathetical process or it may preferably be carried out on an ion exchange resin. The non-toxic pharmaceutically acceptable salts are preferred, although other salts may be useful, e.g. in isolating or purifying the product.

Novel intermediates form a further aspect of the invention.

The compounds of the invention have been submitted to the assay outlined below and have been found to be P2 7-TM G-protein coupled receptor antagonists, particularly to the $P2Y_2$ receptor. Accordingly they are useful in therapy and are, in particular, indicated for use as anti-inflammatory agents useful in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. The compounds of the invention can be co-administered with other anti-inflammatory agents. ATP receptors have also been reported on tumour cells and may be involved in the development of cancer. Antagonists may therefore be useful in treatment of cancer.

The invention provides in a further aspect a method of treating an inflammatory condition which comprises administering to a patient in need of therapy, a therapeutically effective amount of a compound of the invention.

According to the invention there is further provided use of the compounds of the invention in the manufacture of a medicament for use in the treatment of an inflammatory condition.

The compounds may be administered orally, topically e.g. to the lung and/or the airways, in the form of solutions, suspensions, HFA areosols and dry powder formulations, e.g. Turbuhaler® formulations or by parenteral administration in the form of sterile parenteral solutions or suspensions.

The invention further provides a pharmaceutical composition comprising a compound according to the present invention in association with a pharmaceutically acceptable excipient and/or adjuvant. Particularly preferred are compositions not containing material capable of causing an adverse, e.g. an allergic, reaction. For example a chelating or sequestering agent, an antioxidant, a tonicity adjusting agent, a pH modifying agent and/or a buffering agent are suitable additives.

The compounds of the invention may also be administered by means of a dry powder inhaler. The inhaler may be a single or a multi dose inhaler, and may be a breath actuated dry powder inhaler.

A pharmaceutical composition according to the present invention could optionally be prepared in freeze dried form using any lyophilisation techniques commonly used within the pharmaceutical area. Upon use but before administration, such pharmaceutical compositions are generally reconstituted in a pharmaceutically acceptable excipient. Preferably a solution of the pharmaceutical composition according to the invention obtained after reconstitution is an isotonic solution. Such a pharmaceutical composition according to the present invention when reconstituted is preferably administered by injection, for example intravenously, subcutaneously or intramuscularly.

The invention is illustrated by the following examples. In the examples the NMR spectra were measured on a Varian Unity Inova 300 or 400 MHz spectrometer and the MS spectra measured as follows: EI spectra were obtained on a VG 70-250S or Finnigan Mat Incos-XL spectrometer, ESI and APCI spectra were obtained on Finnigan Mat SSQ7000 or a Micromass Platform spectrometer. Where necessary, the reactions were performed under an inert atmosphere of either nitrogen or argon. Where necessary, preparative HPLC separations were generally performed using a Novapak®, Bondapak®, or Hypersil® column packed with BDSC-18 reverse phase silica gel. Chromatography was generally performed using Matrex Silica 60®1(35–70 micron)or Prolabo Silica gel 60® (35–75 micron) suitable for flash silica gel chromatography.

EXAMPLE 1

2-[[5-{5H-Dibenzo[a,d]cyclohepten-5-yl}-3,4-dihydro-2-oxo-4-thioxo-1(2H)-pyrimidinyl]methyl]-4-thiazolecarboxylic acid i) 5-Bromo-2,4-bis(1,1-dimethylethoxy)pyrimidine To a solution of potassium tert-butoxide (67.5 g) in tetrahydrofuran (500 ml) was added 5-bromo-2,4-dichloropyrimidine (55 g) (J. Am. Chem. Soc. 1934, 56, 134) in tetrahydrofuran (100 ml) dropwise. After 1.5 hours, water (100 ml) was added carefully and the mixture extracted with ethyl acetate. The combined organic solution was washed with water, dried ($MgSO_4$) and evaporated under reduced pressure. Purification was by chromatography eluting with 5% triethylamine in isohexane to give the product as a solid. Yield 52.4 g

MS: GC-MS: 304/302 ($M^+$)

ii) 2-Bromomethyl-4-thiazolecarboxylic acid, ethyl ester

2-Methyl-4-thiazolecarboxylic acid ethyl ester (1 g) (Liebigs Ann. Chem. 1981, 623), N-bromosuccinimide (1.04 g) and a catalytic amount of benzoyl peroxide in chloroform (25 ml) was heated at reflux for 20 hours. After cooling, the reaction mixture was washed with saturated aqueous sodium bicarbonate, dried ($MgSO_4$) and evaporated under reduced pressure. Purification was by chromatography eluting with 40% ethyl acetate in isohexane to give the product as an oil. Yield 0.5 g.

MS: GC-MS: 249/251 ($M^+$)

iii) 5-{5H-Dibenzo[a,d]cyclohepten-5-yl)-2,4(1H,3H)-pyrimidinedione

To a solution of the product of step (i) (50 g) in dry tetrahydrofuran (11) at −78° C. was added n-butyllithium (69 ml of a 2.5M solution in hexane) dropwise such that the internal temperature of the reaction did not rise above −65° C. After 0.5 hours a solution of 5H-dibenzo[a,d] cyclohepten-5-one (44 g) in tetrahydrofuran (100 ml) was added. The reaction mixture was stirred at −78° C. for three hours and then allowed to warm to room temperature overnight. Saturated aqueous ammonium chloride solution (400 ml) was added and the mixture extracted with ethyl acetate. The organic solution was dried ($MgSO_4$) and evaporated under reduced pressure to give the crude 5-{2,4-bis(1,1-dimethylethoxy)pyrimidin-5-yl)-5H-dibenzo[a,d]cyclohepten-5-ol which was used directly. To a stirred solution of this product and triethylsilane (64 ml) in dry dichloromethane (400 ml) cooled in an ice-bath was added trifluoroacetic acid (150 ml) dropwise over ten minutes. The cooling bath was removed and the solution was stirred at room temperature overnight. Toluene (300 ml) was added and solution was evaporated under reduced pressure. The residue was azeotroped with toluene (3 times). The oil was treated with diethyl ether and the precipitated product collected as a white powder. Yield 44 g.

MS: EI: 302 ($M^+$,100%)

iv) 2-[[5-{5H-Dibenzo[a,d]cyclohepten-5-yl}-3,4-dihydro-2,4-dioxo-1(2H)-pyrimidinyl]methyl]-4-thiazolecarboxylic acid, ethyl ester To a slurry of the product of step (iii) (1.1 g) in dry 1,2-dichloroethane (20 ml) was added bis(trimethylsilyl)trifluoroacetamide (1.9 ml) under nitrogen. The mixture was heated under reflux for 1 hour until the mixture became a homogeneous solution. The solution was allowed to cool to room temperature and a solution of the product of step (ii) (0.83 g) in dry acetonitrile (10 ml) was added. The solution was then heated at reflux for 7 hours. The reaction mixture was allowed to cool and evaporated under reduced pressure. Purification was by chromatography eluting with 30% ethyl acetate in toluene. The resulting oil was triturated with diethyl ether/isohexane to give the product as a cream solid. Yield 1.52 g.

MS: FAB(+ve): 472 (M+1, 100%)

v) 2-[[5-{5H-Dibenzo[a,d]cyclohepten-5-yl}-3,4-dihydro-2-oxo-4-thioxo-1(2H)-pyrimidinyl]methyl]-4-thiazolecarboxylic acid, ethyl ester A mixture of the product of step (iv) (2.1 g) and Lawesson's reagent (1.78 g) in dry 1,4-dioxane (36 ml) was heated at reflux for 16 hours. After cooling, the reaction mixture was diluted with ethyl acetate and washed with water. The organic layer was dried $MgSO_4$) and evaporated under reduced pressure. Purification was by chromatography eluting with 50% ethyl acetate in isohexane. Yield 1.5 g.

MS: FAB(+ve): 488 (M+1)

vi) 2-[[5-{5H-Dibenzo[a,d]cyclohepten-5-yl}3,4-dihydro-2-oxo-4-thioxo-1(2H)pyrimidinyl]methyl]-4-thiazolecarboxylic acid A mixture of the product of step (v) (1.5 g) and lithium hydroxide monohydrate (1.26 g) in methanol (100 ml) and water (50 ml) was stirred at room temperature overnight. The solution was concentrated under reduced pressure to 50 ml and the pH adjusted to 3.5 with 2M hydrochloric acid. The precipitated product was collected, washed with water and dried. Yield 1.1 g.

MS: FAB(+ve): 460 (M+1)

1H NMR: δ (DMSO) 13.19(br s,1H), 12.75(s,1H), 8.5(s, 1H), 7.6–7.2 (m,8H), 7.1(s,1H), 6.86(s,2H), 5.82(s,1H), 5.2(s,2H).

MP: 228° C.

EXAMPLE 2

2-[[5-{5H-Dibenzo[a,d]cyclohepten-5-yl}-3,4-dihydro-2-oxo-4-thioxo-1(2H)-pyrimidinyl]methyl]-5-thiazolecarboxlic acid i) 2-Bromomethyl-5-thiazolecarboxylic acid, ethyl ester 2-Methyl-5-thiazolecarboxylic acid ethyl ester (3.9 g) (J. Am. Chem. Soc. 1982, 104, 4461), N-bromosuccinimide (4.1 g) and catalytic azoisobutyronitrile in ethyl acetate (150 ml) was heated at reflux and under a 500 W halogen lamp for 16 hours. The solution was washed with water, dried ($MgSO_4$) and evaporated. Purification was by chromatography eluting with 50% ethyl acetate in isohexane. Yield 1.5 g.

MS: GC-MS: 249/251 ($M^+$)

ii) 2-[[5-{5H-Dibenzo[a,d]cyclohepten-5-yl}-3,4-dihydro-2,4-dioxo-1(2H)-pyrimidinyl]methyl]-5-thiazolecarboxylic acid, ethyl ester The subtitle compound was prepared from the product of example 1 step (iii) (1.0 g) and 2-(bromomethyl)-5- thiazolecarboxylic acid ethyl ester (0.9 g) according to the method of example 1 step (iv). The reaction mixture was evaporated to dryness under reduced pressure and the crude product was recrystallised from ethyl acetate/methanol. Yield 0.78 g.

1H NMR: δ (DMSO) 11.38 (s,1H), 8.36 (s,1H), 7.55 (d,2H), 7.36 (m,4H), 7.28 (m,2H), 6.85 (s,2H), 6.78 (s,1H), 5.34 (s,1H), 5.16 (s,2H), 4.32 (q,2H), 1.31(t,3H).

iii) 2-[[5-{5H-Dibenzo[a,d]cyclohepten-5-yl}-3,4-dihydro-2-oxo-4-thioxo-1(2H)-pyrimidinyl]methyl]-5-thiazolecarboxylic acid, ethyl ester The subtitle compound was prepared from the product of step (ii) (0.77 g) according to the procedure of example 1 step (v). Yield 0.56 g.

1H NMR: δ (DMSO) 12.75 (s,1H), 8.41 (s,1H), 7.61 (d,2H), 7.36 (m,5H), 7.28 (m,3H), 7.12 (s,1H), 6.87 (s,2H), 5.83 (s,1H), 5.26 (s,2H) 4.33 (q,2H), 1.31 (t,3H).

iv) 2-[[5-{5H-Dibenzo[a,d]cyclohepten-5-yl}-3,4-dihydro-2-oxo-4-thioxo-1(2H)-pyrimidinyl]methyl]-5-thiazolecarboxylic acid The title compound was prepared from the product of step (iii) (0.56 g) according to the procedure of example 1 step (vi). After the reaction was complete the aqueous solution was washed with ethyl acetate, acidified and extracted with ethyl acetate. The ethyl acetate extracts were dried (MgSO$_4$) and evaporated. Purification was by reverse phase preparative HPLC. Yield 0. 197 g.

MS: ESI(+ve): 460 (M+1, 100%)

1H NMR: δ (DMSO) 7.89 (s, 1H), 7.6 (d, 2H), 7.35 (m, 4H), 7.27 (m, 2H), 7.09 (s, 1H), 6.84 (s, 2H), 5.83 (s, 1H), 5.15 (s, 2H).

MP: 198–200° C.

EXAMPLE 3

2-[[5-{5H-Dibenzo[a,d]cyclohepten-5-yl}-3,4-dihydro-2-oxo-4-thioxo-1(2H)-pyrimidinyl]methyl]-4-oxazolecarboxylic acid (i) 2-[[5-{5H-Dibenzo[a,d]cyclohepten-5-yl}-3,4-dihydro-2,4-dioxo-1(2H pyrimidinyl]methyl]-4-oxazolecarboxylic acid, ethyl ester The subtitle compound was prepared from the product of example 1 step (iii) (0.69 g) and 2-bromomethyl-4-oxazolecarboxylic acid ethyl ester (J. Org. Chem. 1992, 57, 4797) (0.62 g) according to the method of example 1 step (iv). Yield 0.69 g.

1H NMR: δ (DMSO) 11.36 (s, 1H), 8.87 (s, 1H), 7.56 (d, 2H), 7.27–7.39 (m, 6H), 6.88 (s, 2H), 6.76 (s, 1H), 5.34 (s, 1H), 5.01 (s, 2H), 4.3 (q, 2H), 1.31 (t, 3H).

ii) 2-[[5-15H-Dibenzo[a,d]cyclohepten-5-yl}-3,4-dihydro-2-oxo-4-thioxo-1(2H)-pyrimidinyl]methyl]-4-oxazolecarboxylic acid, ethyl ester The subtitle compound was prepared from the product of step (i) (0.69 g) according to the method of example 1 step (v). Purification was by chromatography eluting with 50% ethyl acetate in isohexane. Yield 0.34 g.

1H NMR: δ (DMSO) 12.76 (s, 1H), 8.90 (s, 1H), 7.61 (d, 2H), 7.37 (m, 4H), 7.30 (m, 2H), 7.11 (s, 1H), 6.92 (s, 2H), 5.83 (s, 1H), 5.11 (s, 2H), 4.31 (q, 2H), 1.31 (t, 3H).

iii) 2-[[5-{5H-Dibenzo[a,d]cyclohepten-5-yl}-3,4-dihydro-2-oxo-4-thioxo-1(2H)-pyrimidinyl]methyl]-4-oxazolecarboxylic acid The title compound was prepared from the product of step (ii) (0.34 g) according to the method of example 1 step (vi).

After the reaction was complete the aqueous solution was washed with ethyl acetate, acidified and extracted with ethyl acetate. The ethyl acetate extracts were dried (MgSO$_4$) and evaporated. Purification was by reverse phase preparative HPLC. Yield 0.06 g.

MS: LC-MS: 444 (M+1, 100%)

1H NMR: δ (DMSO) 8.28 (s, 1H), 7.61 (m, 2H), 7.35 (m, 4H), 7.28 (m, 2H), 7.08 (s, 1H), 6.91 (s, 2H), 5.83 (s, 1H), 5.01 (s, 2H).

MP: 200° C.

EXAMPLE 4

5-[[5-{5H-Dibenzo[a,d]cyclohepten-5-yl}-3,4-dihydro-2-oxo-4-thioxo-1(2H)-pyrimidinyl]methyl]-2-furancarboxylic acid i) 5-[[5-{5H-Dibenzo[a,d]cyclohepten-5-yl}-3,4-dihydro-2,4-dioxo-1(2H)-pyrimidinyl]methyl]-2-furancarboxylic acid, methyl ester The subtitle compound was prepared from the product of example 1 step (iii) (1.1 g) and 5-bromomethyl-2-furancarboxylic acid methyl ester (0.96 g)(J. Chem. Soc. Perkin Trans. 1, 1981, 1125, Bull. Chem. Soc. Jpn. 1987, 60, 1807) according to the method of example 1 step (iv). Purification was by chromatography eluting with 50–80% ethyl acetate in isohexane. Yield 1.24 g.

MS: APCI(+ve): 441 (M+1,100%)

ii) 5-[[5{-5H-Dibenzo[a,d]cyclohepten-5-yl}-3,4-dihydro-2-oxo-4-thioxo-1(2H)-pyrimidinyl]methyl]-2-furancarboxylic acid, methyl ester The subtitle compound was prepared from the product of step (i) (1.23 g) according to the method of example 1 step (v). Purification was by chromatography eluting with 20–30% ethyl acetate in isohexane. Yield 0.92 g.

MS: APCI(−ve): 455 (M−1)

iii) 5-[[5-{5H-Dibenzo[a,d]cyclohepten-5-yl}-3,4-dihydro-2-oxo-4-thioxo-1(2H)-pyrimidinyl]methyl]-2-furancarboxylic acid The title compound was prepared from the product of step (ii) (0.91 g) according to the method of example 1 step (vi). Yield 0.58 g MS: APCI(+ve): 443 (M+1,100%)

1H NMR: δ (DMSO) 13.27(s,1H), 12.68(s,1H), 7.60(d, 2H), 7.38–7.24(m,7H), 6.96(s,1H), 6.84(s,2H), 6.60(d, 1H), 5.81 (s, 1H), 4.92(s,2H)

MP: 178–180° C.

EXAMPLE 5

5-[5H-Dibenzo[a,d]cyclohepten-5-yl]-3,4-dihydro-1-[4-[1H-tetrazol-5-yl]thiazol-2-ylmethyl]-4-thioxo-2(1H)-pyrimidinone i) 5-[2-Methylthiazol-4-yl]-1H-tetrazole A mixture of 4-cyano-2-methylthiazole (5.74 g) (U.S. Pat. No. 4,010,173 1977), trimethylsilyl azide (10.64 g) and dibutyltin oxide (115 g) in toluene (300 ml) was heated at 120° C. for 24 hours. The reaction mixture was diluted with ethyl acetate and extracted with dilute aqueous sodium hydroxide solution. The combined extracts were acidified to pH 5 with 1M HCl and extracted with ethyl acetate. The extracts were dried (MgSO$_4$) and evaporated. Yield 4.53 g.

MS: APCI(−ve): 166 (M−1, 100%)

ii) A mixture of 2-[2-[Trimethylsilyl]ethoxymethyl]-5-[2-methylthiazol-4-yl]-2H-tetrazole and 1-[2-[Trimethylsilyl] ethoxymethyl]-5-[2-methylthiazol-4-yl]-1H-tetrazole A mixture of the product from step (i) (4.53 g) and potassium carbonate (7.48 g) in DMF (50 ml) was treated with 2-(trimethylsilyl)ethoxymethyl chloride (4.97 g) and stirred overnight. The reaction mixture was poured into water and extracted with diethyl ether. The combined extracts were washed with water, dried (MgSO$_4$) and evaporated. The crude product was purified by chromatography eluting with 50% diethyl ether in isohexane to give a mixture of regioisomers. Yield 7.8 g.

MS: GC-MS: 282 (M−15)

iii) A mixture of 5-[2-bromomethylthiazol-4-yl]-2-[2-[trimethylsilyl]ethoxymethyl]-2H-tetrazole and 5-[2-bromomethylthiazol-4-yl]-1-[2-[trimethylsilyl]ethoxymethyl]1H-tetrazole A mixture of the product from step (ii) (4.5 g), catalytic azoisobutyronitrile and N-bromosuccinimide (2.69 g) in ethyl acetate (100 ml) was irradiated under a 500 W halogen lamp for 4 hours. The mixture was washed with saturated aqueous sodium bicarbonate solution, dried (MgSO$_4$) and evaporated to give an orange oil (2.92 g) which was used directly in the next step.

iv) A mixture of 5-[5H-Dibenzo[a,d]cyclohepten-5-yl]-1-[4-[1-[2-[trimethylsilyl]ethoxymethyl]-1H-tetrazol-5-yl]thiazol-2-ylmethyl]-2,4(1H,3H))-pyrimidinedione and 5-[5H-Dibenzo[a,d]cyclohepten-5-yl]-1-[4-[2-[2-[trimethylsilylethoxylmethyl]-2H-tetrazol-5-yl]thiazol-2-ylmethyl]-2,4(1H,3H)-pyrimidinedione The subtitle compound was prepared from the product of example 1 step (iii) (0.78 g) and the product from step (iii) (2.92 g) according to the method of example 1 step (iv). The reaction was evaporated under reduced pressure and purified by chromatography eluting with 20% ethyl acetate in toluene. Yield 0.53 g. This was used directly in the next step.

v) 5-[5H-Dibenzo[a,d]cyclohepten-5-yl]-3,4-dihydro-l-[4-[H-tetrazol-5-yl]thiazol-2-ylmethyl]-4-thioxo-2(1H)-pyrimidinone The title compound was prepared from the product of step (iv) according to the method of example 1 step (v). Purification was by reverse phase preparative HPLC to give a yellow solid. Yield 0.022 g.

MS: ESI(+ve): 484(M+1,100%); ESI(−ve): 482 (M−1, 100%)

1H NMR: δ (CD$_3$OD) 6.84(d,1H), 6.55(m,1H), 6.46(m, 2H), 6.26(s,1H), 5.93 (s,2H), 5.12(s,1H), 4.46 (s,2H).

MP: 185–192° C.

EXAMPLE 6

4-[[5-{5H-Dibenzo[a,d]cyclohepten-5-yl}-3,4-dihydro-2-oxo-4-thioxo-1(2H)-pyrimidinyl]methyl]-2-thiophenecarboxylic acid i) 4-Bromomethyl-2-thiophenecarboxylic acid, methyl ester A stirred mixture of 4-methyl-2-thiophenecarboxylic acid methyl ester (0.252 g) (Coll. Czechoslov. Commun. 1958, 23, 452, Synth. Commun. 1994, 24, 1721) and N-bromosuccinimide (0.287 g) in benzene (20 ml) was irradiated under a 500 W halogen lamp for 2 hours. The mixture was diluted with ethyl acetate, washed with water and dried (MgSO$_4$). The residue was evaporated and purified by chromatography eluting with 50% ethyl acetate in isohexane. Yield 0.29 g.

1H NMR: δ (CDCl$_3$): 7.80(d,1H), 7.49(brs,1H), 4.64(s, 2H), 3.89(s,3H).

ii) 4-[[5-{5H-Dibenzo[a,d]cyclohepten-5-yl}-3,4-dihydro-2,4-dioxo-1(2H)-pyrimidinyl]methyl]-2-thiophenecarboxylic acid, methyl ester The subtitle compound was prepared from the product of step (i) (0.29 g) and the product of example 1 step (iii) (0.373 g) according to the method of example 1 step (iv). Purification was by chromatography eluting with 10% ethyl acetate in toluene. Yield 0.34 g.

MS: APCI(+ve): 457 (M+1, 100%)

iii) 4-[[5-{5H-Dibenzo[a,d]cyclohepten-5-yl}-3,4-dihydro-2-oxo-4-thioxo-1(2H)-pyrimidinyl]methyl]-2-thiophenecarboxylic acid, methyl ester The subtitle compound was prepared from the product of step (ii) (0.34 g) according to the method of example 1 step (v). Purification was by chromatography eluting with 10% ethyl acetate in toluene. Yield 0.34 g.

MS: APCI(+ve): 473 (M+1,100%)

iv) 4-[[5-{5H-Dibenzo[a,d]cyclohepten-5-yl}-3,4-dihydro-2-oxo-4-thioxo-1(2H)-pyrimidinyl]methyl]-2-thiophenecarboxylic acid The title compound was prepared from the product of step (iii) (0.34 g) according to the method example 1 step (vi). The crude product was purified by reverse phase preparative HPLC to give a yellow powder. Yield 0.044 g.

MS: APCI(+ve): 459 (M+1,100%)

1H NMR: δ (DMSO):7.59(s,1H), 7.57(s,2H), 7.43(d,1H), 7.23–7.37(m,6H) 6.95(s,1H), 6.80(s,2H), 5.81(s,1H), 4.76 (s,2H).

MP: 170–172° C.

EXAMPLE 7

2-[[5-{5H-Dibenzo[a,d]cyclohepten-5-yl}-3,4-dihydro-2-oxo-4-thioxo-1(2H)-pyrimidinyl]methyl]-4-thiazoleacetic acid i) [5-{5H-Dibenzo[a,d]cyclohepten-5-yl}-3,4-dihydro-2,4-dioxo-1(2H)-pyrimidine]acetonitrile The subtitle compound was prepared from the product of example 1 step (iii) (5.0 g) and bromoacetonitrile (1.27 ml) according to the method of example 1 step (iv). Purification was by chromatography eluting with 20–60% ethyl acetate in toluene. Yield 4.4 g.

MS: APCI(−ve): 340 (M−1,100%)

ii) 2-[5-{5H-Dibenzo[a,d]cyclohepten-5-yl}-3,4-dihydro-2,4-dioxo-1(2H)-pyrimidine]ethanethioamide Hydrogen sulphide gas was bubbled through a mixture of the product from step (i) (2.0 g) and triethylamine (10 ml) in dry pyridine (40 ml) for 1.5 hr. The mixture was evaporated and the residue triturated with diethyl ether. Yield 2.26 g.

MS: APCI(+ve): 376 (M+1)

iii) 2-[[5-{5H-Dibenzo[a,d]cyclohepten-5-yl}-3,4-dihydro-2,4-dioxo-1(2H)pyrimidinyl]methyl]-4-thiazoleacetic acid, ethyl ester A mixture of the product from step (ii) (2.0 g) and ethyl 4-chloroacetoacetate (0.72 ml) in ethanol (30 ml) was heated at reflux for 40 hours. The residue after evaporation was partitioned between ethyl acetate and aqueous sodium bicarbonate and filtered. The aqueous phase was neutralised and extracted with ethyl acetate. The extracts were washed with water then brine, dried (Na$_2$SO$_4$) and evaporated. Purification was by chromatography eluting with 60–90% ethyl acetate in isohexane. Yield 0.95 g.

MS: APCI(+ve): 486 (M+1)

iv) 2-[[5-{5H-Dibenzo[a,d]cyclohepten-5-yl}-3,4-dihydro-2-oxo-4-thioxo-1(2H)-pyrimidinyl]methyl]-4-thiazoleacetic acid, ethyl ester The subtitle compound was prepared from the product of step (iii) (0.45 g) according to the method of example 1 step (v). Purification was by chromatography eluting with 30–50% ethyl acetate in isohexane. Yield 0.31 g.

MS: LC-MS: 502 (M+1)

v) 2-[[5-{5H-Dibenzo[a,d]cyclohepten-5-yl}-3,4-dihydro-2-oxo-4-thioxo-1(21)-pyrimidinyl] methyl]-4-thiazoleacetic acid The title compound was prepared from the product of step (iv) (0. 15 g) according to the method of example 1 step (vi). Purification by reverse phase preparative HPLC. Yield 0.027 g.

MS: LC-MS: 474 (M+11)

1H NMR: δ (DMSO) 7.6(d,2H), 7.50(s,1H), 7.4–7.2(m, 6H), 7.07(s,1H), 6.82(s,2H), 5.81(s,1H), 5. 12(s,2H), 3.74 (s,2H).

MP: 169–172° C.

EXAMPLE 8

2-[[5-{2,8-Dimethyl-5H-dibenzo[a,d]cyclohepten-5-yl}-3,4-dihydro-2-oxo-4-thioxo -1(2H)-pyrimidinyl]methyl]-4-thiazolecarboxylic acid i) 5-[2,8-Dimethyl-5H-dibenzo[a,d]cyclohepten-5-yl]-2,4 (1H,3H)-pyrimidinedione n-Butyllithium (5.6 ml of a 2.5M solution in hexanes) was added dropwise to a solution of 5-bromo-2,4-bis(1,1,-dimethylethoxy)pyrimidine (example 1 step (i)) (3.85 g) in tetrahydrofuran (30 ml) at −78° C. The solution was stirred for 30 minutes and a solution of 10,11-dihydro-2,8-dimethyl-5H-dibenzo[a,d]cyclohepten-5-one (European Patent, 1993, 0 589 322 A1) (3.0 g) in tetrahydrofuran (20 ml) was added. The mixture was stirred at −78° C. for 45 minutes and room temperature for 15 minutes and then partitioned between brine and ethyl acetate. The organic phase was dried (MgSO$_4$) and evaporated. The residue was dissolved in glacial acetic acid (100 ml) and heated at 120° C. for 30 minutes. The solvent was evaporated and the residue azeotroped with toluene and triturated with diethyl ether to give a solid. Yield 4.03 g.

MS: APCI(+ve): 331 (M+1,100%)

ii) 2-[[5-{2,8-Dimethyl-5H-dibenzo[a,d]cyclohepten-5-yl}-3,4-dihydro-2,4-dioxo-1(2H)-pyrimidinyl]methyl]-4-thiazolecarboxylic acid, ethyl ester The subtitle compound was prepared from the product of step (i) (0.3 g) according to the method of example 1 step (iv). Purification was by chromatography eluting with 50% ethyl acetate in isohexane. Yield 0.3 g.

1H NMR: δ (DMSO): 11.34(s,1H), 8.52(s,1H), 7.4(d,2H), 7.16(m,4H), 6.74(s,3H), 5.22(s, 1H), 5.13(s,2H), 4.35(q, 2H), 2.27(s,6H), 1.34(t,3H).

iii) 2-[[5-12,8-Dimethyl-5H-dibenzo[a,d]cyclohepten-5-yl}-3,4-dihydro-2-oxo-4-thioxo-1(2H)-pyrimidinyl]methyl]-4-thiazolecarboxylic acid, ethyl ester The subtitle compound was prepared from the product of step (ii) (0.3 g) according to the method of example 1 step (v). Purification was by chromatography eluting with 25–50% ethyl acetate in isohexane. Yield 0.13 g.

MS: LC-MS: 516 (M+1,100%)

iv) 2-[[5-{2,8-Dimethyl-5H-dibenzo[a,d]cyclohepten-5-yl}-3,4-dihydro-2-oxo-4-thioxo-1(2H)-pyrimidinyl]methyl]-4-thiazolecarboxylic acid The title compound was prepared from the product of step (iii) (0.13 g) according to the method of example 1 step (vi). Yield 0.064 g

MS: LC-MS: 488 (M+1,100%)

1H NMR: δ (DMSO) 8.1(s,1H), 7.44(d,2H), 7.13(d,4H), 7.06(s,1H), 6.76(s,2H), 5.72(s,1H), 5.15(s,2H), 2.26(s,6H).

MP: 200–205° C.

EXAMPLE 9

N-[2-[[5-{2,8-Dimethyl-5H-dibenzo[a,d]cyclohepten-5-yl}-3,4-dihydro-2-oxo-4-thioxo-1(2H)-pyrimidinyl]methyl] thiazol-4-ylcarbonyl]-L-aspartic acid i) N-[2-[[5-{2,8-Dimethyl-5H-dibenzo[a,d]cyclohepten-5-yl}-3,4-dihydro-2-oxo4-thioxo-1(2H)-pyrimidinyl]methyl] thiazol-4-ylcarbonyl]-L-aspartic acid, dimethyl ester The product from example 8(0.4 g) was dissolved in dry dimethylformamide (15 ml) and treated with N,N-carbonyldiimidazole (0.16 g). After 30 minutes L-aspartic acid dimethyl ester (0.32 g) was added followed by triethylamine (0.5 ml). The mixture was stirred overnight and partitioned between ethyl acetate and 2M HCl. The organic phase was washed with brine, dried (MgSO$_4$), evaporated and purified by chromatography eluting with 50% ethyl acetate in dichloromethane. Used directly in the next step.

ii) N-[2-[[5-{2,8-Dimethyl-5H-dibenzo[a,d]cyclohepten-5-yl}-3,4-dihydro-2-oxo-4-thioxo-1(2H)-pyrimidinyl]methyl] thiazol-4-ylcarbonyl]-L-aspartic acid The product of step (i) (0.1 g) was converted to the title compound according to the method of example 1 step (vi). Yield 0.035 g.

MS: APCI(+ve): 603 (M+1,100%)

1H NMR: δ (DMSO) 13.0(br s,1H), 12.74(br s,1H), 12.5(br s,1H), 8.56(d,1H), 8.38(s,1H), 7.46(d,2H), 7.20(d, 4H), 7.0(s,1H), 6.76(dd,2H), 5.76(s,1H), 5.23(s,2H), 4.86 (m,1H), 2.90(d,2H), 2.26(s,6H).

MP: 175° C.

EXAMPLE 10

2-[[2-[[5-{2,8-Dimethyl-5H-dibenzo[a,d]cyclohepten-5-yl}-3,4-dihydro-2-oxo-4-thioxo-1(2H)-pyrimidinyl]methyl] thiazol-4-ylcarbonyl]amino]-4-thiazoleacetic acid i) 2-[[2-[[5-{2,8-Dimethyl-5H-dibenzo[a,d]cyclohepten-5-yl}-3,4-dihydro-2-oxo-4-thioxo-1(2H)-pyrimidinyl]methyl] thiazol-4-ylcarbonyl]amino]-4-thiazole acetic acid, ethyl ester The product from example 8(0.11 g) and 2-amino-4-thiazoleacetic acid ethyl ester (0.063 g) were dissolved in dry dimethylformamide (5 ml). Bromo-tris(pyrrolidino)-phosphonium hexafluorophosphate (0.11 g) and triethylamine (0.08 ml) were added and the mixture was stirred at room temperature for 24 hours. The reaction mixture was quenched with brine/HCl and extracted with ethyl acetate. The extract was washed with water, dried (MgSO$_4$) and evaporated. The residue was purified by chromatography eluting with 10% ethyl acetate in dichloromethane and used directly in the next step.

ii) 2-[[2-[[5-{2,8-Dimethyl-5H-dibenzo[a,d]cyclohepten-5-yl}-3,4-dihydro-2-oxo-4-thioxo-1(2N)-pyrimidinyl]methyl] thiazol-4-ylcarbonyl]amino]-4-thiazoleacetic acid The product from step (i) was converted to the title compound according to the method of example 1 step (vi). Yield 0.0227 g.

MS: APCI(+ve): 628 (M+1)

1H NMR: δ (CDCl$_3$): 9.70(br s,1H), 8.31(s,1H), 7.61(d, 2H), 7.14(d,2H), 7.05(s,2H), 6.90(s, 1H), 6.87(s, 1H), 6.69 (s,2H), 5.74(s, 1H), 4.97(s,2H), 3.82(s,2H), 2.08(s,6H).MP:

MP: 200–205° C.

EXAMPLE 11

5-[[5-{2,8-Dimethyl-5H-dibenzo[a,d]cyclohepten-5-yl}-3, 4-dihydro-2-oxo-4-thioxo-1(2H)-pyrimidinyl]methyl]-2-furancarboxylic acid i) 5-[[5-{2,8-Dimethyl-5H-dibenzo[a,d]cyclohepten-5-yl}-3,4-dihydro-2,4-dioxo-1(2H)-pyrimidinyl]methyl]-2-furancarboxylic acid, ethyl ester The subtitle compound was prepared from the product of example 8 step (i) (2.3 g) and 5-bromomethyl-2-furancarboxylic acid ethyl ester (J. Chem. Soc. Perkin Trans. 1, 1981, 1125, Bull. Chem. Soc. Jpn. 1987, 60, 1807) (2.3 g) according to the method of example 1 step (iv). Purification was by chromatography eluting with 25% ethyl acetate in toluene. Yield 1.8 g. Used directly in the next step.

ii) 5-[[5-{2,8-Dimethyl-5H-dibenzo[a,d]cyclohepten-5-yl}-3,4-dihydro-2-oxo-4-thioxo-1(2H)-pyrimidinyl]methyl]-2-furancarboxylic acid ethyl ester The subtitle compound was prepared from the product of step (i) (1.4 g) according to the method of example 1 step (v). Yield 1.15 g. Purification was by chromatography eluting with 10% ethyl acetate in toluene. Used directly in the next step.

iii) 5-[[5-{2,8-Dimethyl-5H-dibenzo[a,d]cyclohepten-5-yl}-3,4-dihydro-2-oxo-4-thioxo-1(2H)-pyrimidinyl] methyl]-2-furancarboxylic acid The title compound was prepared from the product of step (ii) (1.15 g) according to the method of example 1 step (vi). Yield 1.0 g.

MS: APCI(+ve): 471 (M+1)

1H NMR: δ (DMSO) 13.25(br s,1H), 12.63 (br s,1H), 7.45(d,2H), 7.25(d,1H), 7.15(d+s,4H), 6.93(s,1H), 6.74(s, 2H), 6.60(d,1H), 5.72(s,1H), 4.91(s,2H).

MP: 290–292° C.

EXAMPLE 12

5-[[5-{2,8-Dimethyl-5H-dibenzo[a,d]cyclohepten-5-yl-3,4-dihydro-2,4-dioxo-1(2H)-pyrimidinyl]methyl]-2-furancarboxylic acid The product of example 11 step (i) (0.22 g) was converted to the title compound according to the method of example 1 step (vi). Yield 0.16 g.

MS: APCI(+ve): 455 (M+1)

1H NMR: δ (DMSO) 13.20(br s,1H), 11.23(br s,1H), 7.39(d,2H), 7.22(d,1H), 7.16(d,2H), 7.13(s,2H), 6.72(s,2H), 6.60(s,1H), 6.49(d,1H), 5.20(s,1H), 4.84(s,2H), 2.27(s,6H).

MP: 304° C.

EXAMPLE 13

2-[[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]amino]-4-thiazoleacetic acid i) 2-[[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]amino]-4-thiazoleacetic acid, ethyl ester The product of example 11(0.2 g) was converted to the subtitle compound according to the method example 10 step (i), using dichloromethane as reaction solvent. Purification was by chromatography eluting with 30% ethyl acetate in isohexane. Yield 0.17 g.

MS: APCI(+ve): 639 (M+1)

1H NMR: δ (CDCl$_3$) 7.50(d,2H), 7.35(d,1H), 7.10(d,2H), 7.02(s,2H), 6.90(s,1H), 6.85(s,1H), 6.66(s,2H), 6.55(d,1H), 5.77(s,1H), 4.81(s,2H), 4.20(q,2H), 3.82(s,2H), 2.30(s,6H), 1.28(t,3H).

ii) 2-[[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]amino]-4-thiazoleacetic acid The product of step (i) (0.17 g) was converted to the title compound according to the method of example 1 step (vi). Yield 0.1 g.

MS: APCI(+ve): 611 (M+1)

1H NMR: δ (DMSO) 8.32(s,1H), 7.68(d,1H), 7.44(d,2H), 7.15(m,5H), 6.92(s,1H), 6.71(s,2H), 6.67(d, 1H), 5.74(s, 1H), 4.93(s,2H), 3.66(s,2H), 2.22(s,6H).

MP: 210° C.

EXAMPLE 14

2-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonylamino]thiazol-4-yl]acetylamino]-4-thiazoleacetic acid i) 2-[[2-[1,1-Dimethylethoxycarbonylamino]thiazol-4-yl] acetylamino]-4 thiazoleacetic acid, ethyl ester A solution of 2-[[1,1-Dimethylethoxy]carbonylamino]-4-thiazoleacetic acid (1.7 g) (Chem. Pharm. Bull. 1993, 41, 758), 2-amino-4-thiazoleacetic acid ethyl ester (1.35 g), 4-[dimethylamino]pyridine (0.8 g) and bromo-tris (pyrrolidino)phosphonium hexafluorophosphate (3.3 g) in dry dichloromethane (50 ml) was treated with diisopropylethylamine (2.4 ml). The mixture was stirred at room temperature for 16 hours. The reaction mixture was quenched with aqueous sodium bicarbonate and diluted with ethyl acetate. The organic solution was washed with brine and 2M HCl. The solution was dried (MgSO$_4$) and evaporated under reduced pressure. Purification was by chromatography eluting with 30% ethyl acetate in isohexane. Yield 0.8 g.

MS: APCI(+ve): 427 (M+1)

ii) 2-[[2-Aminothiazol-4-yl]acetylamino]4-thiazoleacetic acid, ethyl ester

The product from step (i) (0.8 g) in dry dichloromethane (15 ml) was treated with trifluoroacetic acid (5 ml). After 6 hours at room temperature the mixture was azeotroped with toluene. The residue was dissolved in ethyl acetate and washed with aqueous sodium bicarbonate. The organic solution was dried (MgSO$_4$) and evaporated under reduced pressure. The residue was triturated with ethyl acetate/ isohexanes and filtered. Yield 0.53 g.

MS: APCI(+ve): 327 (M+1)

iii) 2-[[2-[5-[[5-[2,8-Dimethyl-5H-dibenzo[a,d] cyclohepten-5-yl}-3,4-dihydro-2-oxo-4-thioxo-1(2H)-pyrimidinyl]methyl]furan-2-ylcarbonylamino]thiazol-4-yl] acetylamino]-4-thiazoleacetic acid, ethyl ester The product of step (ii) (0.16 g) and example 11(0.2 g) were converted to the subtitle compound according to the method of example 13 step (i). Purification was by chromatography eluting with 50% ethyl acetate in dichloromethane. Yield 0.2 g.

MS: APCI(+ve): 779 (M+1)

iv) 2-[[2-[5-[[5-{2,8-Dimethyl-5H-dibenzo[a,d] cyclohepten-5-yl}-3,4-dihydro-2-oxo-4-thioxo-1(2H)-pyrimidinyl]methyl]furan-2-ylcarbonylamino]thiazol-4-yl] acetylamino]-4-thiazoleacetic acid The product of step (iii) (0.2 g) was converted to the title compound according to the method of example 1 step (vi). Yield 0.08 g.

MS: APCI(+ve): 751 (M+1)

1H NMR: δ (DMSO) 12.63(br s,2H), 12.36(br s,1H), 7.67(d,1H), 7.43(d,2H), 7.12(m,5H), 6.95(s,1H), 6.91(s, 1H), 6.76(s,2H), 6.66(d,1H), 5.76(s,1H), 4.93(s,2H), 3.86(s, 2H), 3.60(s,2H), 2.21(s,6H).

MP: 253° C.

EXAMPLE 15

N-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]-L-aspartic acid i) N-[2-[1,1-Dimethylethoxycarbonylamino]thiazol-4-yl]acetyl-L-aspartic acid, dimethyl ester The subtitle compound was prepared from 2-[1,1-dimethylethoxycarbonylamino]thiazol-4-ylacetic acid (Chem. Pharm. Bull. 1993, 41, 758) (1.0 g) and L-aspartic acid dimethyl ester (1.15 g) according to the method of example 10 step (i). Yield 1.36 g. Used directly in the next step.

ii) N-[2-Aminothiazol-4-yl]acetyl-L-aspartic acid, dimethyl ester

The subtitle compound was prepared from the product of step (i) (1.36 g) according to the method example 14 step (ii). Yield 0.37 g.

MS: APCI(+ve): 302 (M+1); APCI(-ve): 300 (M-1)

iii) N-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]-L-aspartic acid, dimethyl ester A mixture of the product of step (ii) (0.22 g), product of example 11(0.2 g), bromo-tris(pyrrolidino)-phosphonium hexafluorophosphate (0.24 g), 4-dimethylaminopyridine (0.056 g) and N,N-diisopropylethylamine (0.2 ml) in dimethylformamide (5 ml) was stirred at room temperature for 24 hours. The mixture was partitioned between ethyl acetate and brine, washed with saturated aqueous sodium bicarbonate, dilute HCl and brine, dried ($MgSO_4$) and evaporated. Purification was by chromatography eluting with ethyl acetate. Yield 0.24 g.

MS: APCI(+ve): 754 (M+1)

iv) N-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino}thiazol-4-yl]acetyl]-L-aspartic acid The title compound was prepared from the product of step (iii) (0.24 g) according to the method of example 1 step (vi). Yield 0. 12 g.

MS: APCI(+ve): 726 (M+1)

1H NMR: δ (DMSO) 12.64(br s,5H), 8.36(d,1H), 7.67(d, 1H), 7.44(d,2H), 7.12(d,2H), 7.10(s,2H), 6.99(s,1H), 6.90 (s,1H), 6.71(s,2H), 6.66(d,1H), 5.74(s,1H), 4.93(s,2H), 4.57 (q,1H), 3.59(s,2H), 2.64(2xdd,2H), 2.26(s,6H).

MP: 215° C.

EXAMPLE 16

N-Carboxymethyl-N-[[2-[5-[[5-{2,8-dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]glycine i) N-[2-Aminothiazol-4-yl]-N-[ethoxycarbonylmethyl]glycine, ethyl ester The subtitle compound was prepared from 2-[[1,1-dimethylethoxy]carbonylamino]4-thiazoleacetic acid (0.75 g) (Chem. Pharm. Bull. 1993, 41, 758) and diethyl iminodiacetate (0.83 g) according to the method of example 15 step (i) followed by step (ii). Yield 0.91 g.

MS: APCI(+ve): 330 (M+1)

ii) N-Ethoxycarbonylmethyl-N-[[2-[5-[[5-{2,8-dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]glycine, ethyl ester The subtitle compound was prepared from the product of step (i) (0.15 g) and the product of example 11(0.2 g) according to the method of example 15 step (iii) Purification was by chromatography eluting with ethyl acetate. Yield 0.22 g.

MS: APCI(+ve): 782 (M+1)

iii) N-Carboxymethyl-N-[[2-[5-[[5-{2,8-dimethyl-5H-dibenzotadocyclohepten-5-yl]-3,4-dihydro-2-oxo-4-thioxo-1(2H)-pyrimidinyl]methyl]furan-2-ylcarbonylamino]thiazol-4-yl]acetyl]glycine The title compound was prepared from the product of step (ii) (0.22 g) according to the method of example 1 step (vi). Yield 0.11 g.

MS: APCI(+ve): 726 (M+1)

1H NMR: δ(DMSO) 12.70(br s,1H), 12.64(br s,1H), 7.68(d,1H), 7.44(d,2H), 7.10(d,2H), 7.07(s,2H), 7.02(s,1H), 6.91(s,1H), 6.70(s,2H), 6.67(d,1H), 5.73(s,1H), 4.93(s,2H), 4.27(s,2H), 3.99(s,2H), 3.75(s,2H), 2.27(s,6H).

MP: 215° C.

EXAMPLE 17

2-[[5-{2,8-Dibromo-5H-dibenzo[a,d]cyclohepten-5-yl}-3, 4-dihydro-2-oxo-4-thioxo-1(2H)-pyrimidinyl]methyl]-4-thiazolecarboxylic acid i) 4-Bromo-2-bromomethylbenzoic acid, methyl ester The subtitle compound was prepared from 4-bromo-2-methylbenzoic acid methyl ester (22.5 g) according to the method of example 2 step (i). Yield 26.45 g. Used directly in the next step.

ii) [[5-Bromo-2-methoxycarbonylphenyl]methyl]triphenylphosphonium bromide

The product of step (i) (26.45 g) and triphenylphosphine (11.7 g) in acetonitrile (100 ml) was heated under reflux for 1.5 hours. The solvent was evaporated and the residue triturated with diethyl ether. The precipitate was collected. Yield 22.8 g. Used directly in the next step.

iii) 4-Bromo-2-[2-[3-bromophenyl]ethenyl]benzoic acid

The product of step (ii) (22.8 g). 3-bromobenzaldehyde (4.5 ml) and 1,5-diazabicyclo[4.3.0]non-5-ene (DBN) (5.95 g) in acetonitrile (50 ml) was heated under reflux for 0.5 hours. The solution was evaporated under reduced pressure. The residue was dissolved in dichloromethane, washed with 2M HCl, dried ($MgSO_4$) and evaporated. The residue and potassium hydroxide (5.6 g) in water (100 ml) and methanol (20 ml) was heated under reflux for 8 hours. The reaction mixture was diluted with water and washed with dichloromethane. The aqueous solution was acidified to pH 1 (2N HCl) and extracted with dichloromethane. The organic solution was dried ($MgSO_4$), evaporated and the product purified by chromatography eluting with toluene. Yield 8.5 g. Used directly in the next step.

iv) 4-Bromo-2-[2-[3-bromophenyl]ethenyl]benzoic acid

The product from step (iii) (8.5 g) and platinum(iv)oxide (0.87 g) in toluene (150 ml) was stirred under 1 atmosphere of hydrogen for 72 hours. The mixture was filtered and the filtrate evaporated under reduced pressure. Yield 6. 1 g.

MS: APCI(−ve): 381/383/385 (M−1)

v) 2,8-Dibromo-10,11-dihydro-5H-dibenzo[a,d]cyclohepten-5-one

A mixture of the product of step (iv) (6.1 g), polyphosphoric acid (30 ml) and sulpholane (20 ml) was heated at 200° C. for 30 minutes. The cooled mixture was partitioned between ethyl acetate and ice/water. The organic phase was dried (MgSO$_4$) and evaporated under reduced pressure. Purification was by chromatography eluting with 50% toluene in isohexane. Yield 2.71 g.

MS: GC-MS: 364/366/368 (M)

vi) 2,8-Dibromo-5H-dibenzo[a,d]cyclohepten-5-one

The product of step (v) (2.61 g), N-bromosuccinimde (1.5 g) in ethyl acetate (40 ml) was heated at reflux and under a 500 W halogen lamp for 4 hours. After cooling triethylamine (2 ml) was added and the mixture stirred at ambient temperature for 72 hours. The precipitate was collected and partitioned between water and chloroform. The organic solution was washed with brine, dried (MgSO$_4$) and evaporated under reduced pressure. Yield 1.53 g.

MS: GC-MS: 362/364/366 (M)

vii) 5-[2,8-Dibromo-5H-dibenzo[a,d]cyclohepten-5-yl]-2,4(1H,3H).pyrimidinedione

The subtitle compound was prepared from the product of example 1 step (i) (1.15 g) and the product of step (vi) (1.38 g) according to the method of example 1 step (iii). Yield 1.52 g.

MS: APCI(−ve): 461/459/457 (M−1)

viii) 2-[[5-{2,8-Dibromo-5H-dibenzo[a,d]cyclohepten-5-yl}-3,4-dihydro-2,4-dioxo-1(2H)-pyrimidinyl]methyl]-4-thiazolecarboxylic acid, ethyl ester The subtitle compound was prepared from the product of step (vii) (0.99 g) according to the method of example 1 step (iv). Purification was by chromatography eluting with 30% ethyl acetate in toluene. Yield 0.63 g.

MS: APCI(+ve): 632/630/628 (M−1)

ix) 2-[[5-{2,8-Dibromo-5H-dibenzo[a,d]cyclohepten-5-yl}-3,4-dihydro-2-oxo-4-thioxo-1(2H)-pyrimidinyl]methyl]-4-thiazolecarboxylic acid, ethyl ester The subtitle compound was prepared from the product of step (viii) (0.63 g) according to the method of example 1 step (v). Purification was by chromatography eluting with 25–60% ethyl acetate in toluene. Yield 0.21 g.

MS: APCI(+ve): 648/646/644 (M+1)

x) 2-[[5-{2,8-Dibromo-5H-dibenzo[a,d]cyclohepten-5-yl}-3,4-dihydro-2-oxo-4-thioxo-1(2H)-pyrimidinyl]methyl]-4-thiazolecarboxylic acid The title compound was prepared from the product of step (ix) (0.2 g) according to the method of example 1 step (vi). The product was purified by reverse phase preparative HPLC. Yield 0.08 g.

MS: APCI(+ve): 620/618/616 (M+1)

1H NMR: δ (DMSO) 8.14(s,1H), 7.6–7.5(m,6H), 7.1(brs, 1H), 6.94(s,2H), 5.75(s,1H), 5.20(s,2H).

MP: 215–217° C.

EXAMPLE 18

(±)-5-[[3,4-Dihydro-5-{2,3,8-trimethyl-5H-dibenzo[a,d]cyclohepten-5-yl}-2-oxo-4-thioxo-1(2H)-pyrimidinyl]methyl]-2-furancarboxylic acid i) 2,4,5-Trimethylbenzoic acid n-Butyllithium (100 ml of a 2.5M solution in hexanes) was added to a solution of 5-bromo-1,2,4-trimethylbenzene (50 g) in tetrahydrofuran (600 ml) at −70° C. After 1.5 hours the solution was warmed to −40° C. then cooled to −70° C. Carbon dioxide gas was bubbled through the solution for 10 minutes and the mixture was allowed to warm to room temperature. The solvent was evaporated and the residue partitioned between water and isohexane. The aqeous layer was acidified to pH 1 and extracted with dichloromethane. The organic solution was dried (MgSO$_4$) and evaporated under reduced pressure. Yield 36.7 g.

1H NMR: δ (CDCl$_3$) 7.85(s, 1H), 7.04(s, 1H), 2.59(s, 3H), 2.28(s, 3H), 2.27(s, 3H)

ii) 2-[2-[3-Methylphenyl]ethyl]-4,5-dimethylbenzoic acid

A solution of the product of step (i)(36.7 g) in tetrahydrofuran (300 ml) was added dropwise to a stirred solution of lithium diisopropylamide (235 ml of a 2.0M solution in heptane) at 10–20° C. The mixture was allowed to warm to room temperature and stirred for 30 minutes then cooled to −20° C. A solution of 3-methylbenzylbromide (36.2 ml) in tetrahydrofuran (100 ml) was added dropwise over 20 minutes. The mixture was allowed to warm to room temperature and stirred for 45 minutes before quenching with 2M HCl and adding ethyl acetate. The organic phase was washed with brine, dried (MgSO$_4$) and concentrated under reduced pressure to 200 ml. Isohexane (200 ml) was added and the crystallised unreacted starting material filtered off. The filtrate was evaporated and the residue partitioned between 2M sodium hydroxide and isohexane. The aqueous phase was acidified to pH 1 with 2M HCl and extracted with dichloromethane. The extract was dried (MgSO$_4$) and evaporated under reduced pressure. Used directly in the next step.

iii) 10,11-Dihydro-2,3,8-trimethyl-5H-dibenzo[a,d]cyclohepten-5-one

The product from step (ii) was converted to the subtitle compound according to the method of example 17 step (v). Purification was by chromatography eluting with 5% ethyl acetate in isohexane. Yield 2.43 g.

MS: GC-MS: 250 (M, 100%)

iv) ()-5-[2,3,8-Trimethyl-5H-dibenzo[a,d]cyclohepten-5-yl]-2,4(1H,3H)-pyrimidinedione The subtitle compound was prepared from the product from step (iii) (2.4 g) according to the method of example 8 step (i). The residue was purified by chromatography eluting with 5% methanol in chloroform. Yield 1.15 g.

MS: APCI(+ve): 345 (M+1, 100%)

v) (±)-5-[2,3,8-trimethyl-5H-dibenzo[a,d]cyclohepten-5-yl}-2,4-dioxo-1(2H)-pyrimidinyl]methyl]-furancarboxylic acid, ethyl ester The subtitle compound was prepared from the product of step (iv) (1.0 g) and 5-chloromethylfuran-2-carboxylic acid ethyl ester (J. Chem. Soc. Perkin Trans. 1, 1981, 1125, Bull. Chem. Soc. Jpn. 1987, 60, 1807) (0.54 ml) according to the method of example 1 step (iv). Purification was by chromatography eluting with 50% ethyl acetate in isohexane. Yield 0.44 g.

1H NMR: δ (DMSO) 11.24(s,1H), 7.37(d,1H), 7.30(d,)H), 7.25(s,1H), 6.68–6.51(m,4H), 5.16(s, 1H), 4.85(m,2H), 4.34(q,2H), 2.26(s,3H), 2.22(s,3H), 2.18(s,3H), 1.33(t,3H).

vi) (±)-5-[[3,4-Dihydro-5-{2,3,8-trimethyl-5H-dibenzo[a,d]cyclohepten-5-yl}-2oxo-4-thioxo-1(2H)-pyrimidinyl]methyl]-2-furancarboxylic acid, ethyl ester The subtitle compound was prepared from the product of step (v) (0.43 g) according to the method of example 1 step (v). Purification was by chromatography eluting with 20% ethyl acetate in isohexane. Yield 0.27 g.

MS: APCI(+ve): 513 (M+1)

vii) (±)-5-[[3,4-Dihydro-5-{2,3,8-trimethyl-5H-dibenzo[a,d]cyclohepten-5-yl}-2-oxo-4-thioxo-1(2H)-pyrimidinyl]methyl]-2-furancarboxylic acid The title compound was prepared from the product of step (vi) (0.26 g) according to the method of example 1 step (vi). Yield 0. 129 g.

MS: APCI(+ve): 485 (M+1, 100%)

1H NMR: δ (DMSO) 13.23(br s,1H), 12.63(s,1H), 7.46 (d,1H), 7.28(s,1H), 7.24(d,1H), 7.13–7.07(m,3H), 6.92(s, 1H), 6.68(m,2H), 6.59(d,1H), 5.70(s,1H), 4.88(q,2H), 2.25 (s,3H), 2.21 (s,3H), 2.18(s,3H).

MP: 292° C.

EXAMPLE 19

2-[[5-{2,8-Diethyl-5H-dibenzo[a,d]cyclohepten-5-yl}-3,4-dihydro-2-oxo-4-thioxo-1(2H)-pyrimidinyl]methyl]-4-thiazolecarboxylic acid i) 2,8-Diethyl-5H-dibenzo[a,d]cyclohepten-5-one A solution of the product of example 17 step (vi), tetraethyltin (12.8 g) and tetrakis(triphenylphosphine)palladium (O) (0.63 g) in dry dimethylformamide was heated at 116° C. for 48 hours. The mixture was diluted with ethyl acetate, washed with water and brine, dried (MgSO$_4$) and evaporated under reduced pressure. Purification was by chromatography eluting with 30% toluene in isohexane. Yield 1.5 g.

1H NMR: δ (DMSO) 8.07(d,2H), 7.57(d,2H), 7.48(dd, 2H), 7.12(s,2H), 2.75(q,4H), 1.24(t,6H).

ii) 5-[2,8-Diethyl-5H-dibenzo[a,d]cyclohepten-5-yl]-2,4 (1H,3H)-pyrimidinedione

The subtitle compound was prepared from the product of step (i) (1.5 g) according to the method of example 1 step (iii). Yield 1.1 g.

1H NMR: δ (DMSO) 10.92(d, 1H), 10.40(dd, 1H), 7.40 (d,2H), 7.30–7.10(m,4H), 6.89(s,2H), 6.35(d,1H), 5.20(s, 1H), 2.58(q,4H), 1.16(t,6H).

iii) 2-[[5-{2,8-Diethyl-5H-dibenzo[a,d]cyclohepten-5-yl}-3,4-dihydro-2,4-dioxo-1(2H)-pyrimidinyl]methyl]-4-thiazolecarboxylic acid ethyl ester The subtitle compound was prepared from the product of step (ii) (1.0 g) according to the method of example 1 step (iv). Purification was by chromatography eluting with 30% ethyl cetate in toluene. Yield 0.87 g.

1H NMR: δ (DMSO) 11.35(s,1H), 8.52(s,1H), 7.41(d, 2H), 7.20(m,2H), 7.14(s,2H), 6.78(s,3H), 5.24(s, 1H), 5.13 (s,2H), 4.34.(q,2H), 2.57(q,4H), 1.34(t,3H), 1.15(t,6H).

iv) 2-[[5-{2,8-Diethyl-5H-dibenzo[a,d]cyclohepten-5-yl}-3,4-dihydro-2-oxo-4-thioxo-1(2H)-pyrimidinyl]methyl]-4-thiazolecarboxylic acid, ethyl ester The subtitle compound was prepared from the product of step (iii) (0.87 g) according to the method of example 1 step (v). Purification was by chromatography eluting with 15% ethyl acetate in toluene. Yield 0.7 g.

1H NMR: δ (DMSO) 12.73(s,1H), 8.56(s,1H), 7.47(d, 2H), 7.2–7.1(m,7H), 6.80(s,2H), 5.75(s, 1H), 5.21 (s,2H), 4.36(q,2H), 2.57(q,4H), 1.35(t,3H), 1.14(t,6H).

v) 2-[[5{-2,8-Diethyl-5H-dibenzo[a,d]cyclohepten-5-yl}-3,4-dihydro-2-oxo4-thioxo-1(2H)-pyrimidinyl]methyl]-4-thiazolecarboxylic acid The title compound was prepared from the product of step (iv) (0.7 g) according to the method of example 1 step (vi). Yield 0.36 g.

MS: APCI(+ve): 516 (M+1) 1H NMR: δ (DMSO) 12.73 (br s,1H), 8.40(s,1H), 7.47(d,2H), 7.17(dd,2H), 7.15–7.10 (m,3H), 6.80(s,2H), 5.76(s,1H), 5.20(s,2H), 2.56(q,4H), 1.14(t,6H).

MP: 162–165° C.

EXAMPLE 20

(±)-2-[[3,4-Dihydro-5-{2-methoxymethyl-8-methyl-5H-dibenzo[a,d]cyclohepten-5-yl}-2-oxo-4-thioxo-1(2H)-pyrimidinyl]methyl]-4-thiazolecarboxylic acid i) 2,8-Dimethyl-5H-dibenzo[a,d]cyclohepten-5-one 10,11-Dihydro-2,8-dimethyl-5H-dibenzo[a,d] cyclohepten-5-one (European Patent, 1993, 0 25 589 322 A1) (6 g) and N-bromosuccinimide (5 g) in ethyl acetate (100 ml) was irradiated with a 500 W halogen lamp. After 5 hours the reaction mixture was cooled and quenched with brine. The organic layer was collected, dried (MgSO$_4$) and evaporated under reduced pressure. The residue was dissolved in dry dimethylformamide, treated with 1,5-diazabicyclo[4.3.0]non-5-ene (3.5 ml) and heated at 80° C. for 0.25 hours. The cooled reaction mixture was washed with 2M HCl, brine, dried (MgSO$_4$) and evaporated under reduced pressure. Purification was by chromatography eluting with toluene. Yield 4.5 g.

1H NMR: δ (CDCl$_3$) 8.2(d, 2H), 7.37(d+s, 4H), 7.0(s, 2H), 2.47(s, 6H)

ii) 2-Bromomethyl-8-methyl-5H-dibenzo[a,d]cyclohepten-5-one

The product of step (i) (2.0 g) and N-bromosuccinimide (1.52 g) in ethyl acetate (80ml) was irradiated with a 500 W halogen lamp for 4 hours. The reaction mixture was washed with brine, dried (MgSO$_4$) and evaporated under reduced pressure. Purification was by chromatography eluting with toluene. Used directly in the next step.

iii) 2-Methoxymethyl-8-methyl-5H-dibenzo[a,d] cyclohepten-5-one Sodium hydride (0.2 g, 60% dispersion in oil) was added to a solution of the product from step (ii) (1.74 g) in methanol (50 ml) and tetrahydrofuran (20 ml) at 0° C. The mixture was stirred at room temperature for 24 hours and then partitioned between brine and ethyl acetate. The organic phase was washed with brine, dried (MgSO$_4$) and evaporated under reduced pressure. Purification was by chromatography eluting with 5% ethyl acetate in toluene. Yield 0.55 g.

1H NMR: δ (CDCl$_3$) 8.26(d,1H), 8.18(d,1H), 7.50(d+s, 2H), 7.40(d+s,2H), 7.05(dd,2H), 4.58(s,2H), 3.44(s,3H), 2.47(s,3H).

iv) (±)-5-[2-Methoxymethyl-8-methyl-5H-dibenzo[a,d] cyclohepten-5-yl]-2,4(1H,3H)-pyrimidinedione The subtitle compound was prepared from the product of step (iii) (0.5 g) according to the method of example 1 step (iii). Yield 0.64 g. Used directly in the next step.

v) (±)-2-[[3,4-Dihydro-5-{2-methoxymethyl-8-methyl-5H-dibenzo[a,d]cyclohepten-5-yl}-2,4-dioxo-1(2H)-pyrimidinyl]methyl]-4-thiazolecarboxylic acid, ethyl ester The subtitle compound was prepared from the product of step (iv) (0.64 g) according to the method of example 1 step (iv). Purification was by chromatography eluting with 30–50% ethyl acetate in toluene. Yield 0.68 g. Used directly in the next step.

vi) (±)-2-[[3,4-Dihydro-5-{2-methoxymethyl-8-methyl-5H-dibenzo[a,d]cyclohepten-5-yl}-2-oxo-4-thioxo-1(2H)-pyrimidinyl]methyl]-4-thiazolecarboxylic acid, ethyl ester The subtitle compound was prepared from the product of step (v) (0.68 g) according to the method of example 1 step (v). Purification was by chromatography eluting with 20% ethyl acetate in toluene. Yield 0.62 g. Used directly in the next step.

vii) (±)-2-[[3,4-Dihydro-5-)2-methoxymethyl-8-methyl-5H-dibenzo[a,d]cyclohepten-5-yl}-2-oxo-4-thioxo-1(2H)-pyrimidinyl]methyl]-4-thiazolecarboxylic acid The title compound was prepared from the product of step (vi) (0.6 g) according to the method of example 1 step (vi). Yield 0.19 g.

MS: APCI(+ve): 518 (M+1) 1H NMR: δ (DMSO) 8.44 (s,1H), 7.58(d,1H), 7.47(d,1H), 7.30(d+s,2H), 7.15(d+s+s, 2H), 6.86(q,2H), 5.77(s,1H), 5.19(s,2H), 4.37(s,2H), 3.25(s, 3H), 2.29(s,3H).

MP: 140° C.

EXAMPLE 21

(±)-5-[[3,4-Dihydro-5-{3-methoxy-2,8-dimethyl-5H-dibenzo[a,d]cyclohepten-5-yl}-2,4-dioxo-1(2H)-pyrimidinyl]methyl]-2-furancarboxylic acid i) 4,5-Dihydro-4,4-dimethyl-2-[2,4-dimethylphenyl]oxazole Dimethylformamide (8 drops) was added to a stirred suspension of 2,4-dimethylbenzoic acid (80 g) in thionyl chloride (400 ml) and the mixture was stirred overnight at room temperature. The solution was heated at 80° C. for 3 hours and the thionyl chloride evaporated. The residue was dissolved in dichloromethane (200 ml) and added dropwise to a solution of 2-amino-2-methyl-propan-1-ol (124 ml) in dichloromethane (400 ml). The mixture was stirred overnight, washed with 2M HCl, water, aqueous sodium bicarbonate and water. The organic phase was dried (MgSO$_4$) and evaporated. The residue was dissolved in dichloromethane (800 ml) and treated with thionyl chloride (125 ml) dropwise at 0° C. The mixture was stirred at room temperature for 2 hours and evaporated. The solid residue was partitioned between ethyl acetate and aqueous sodium bicarbonate. The organic phase was washed with water, dried (MgSO$_4$) and evaporated. Yield 69 g.

1H NMR: δ (CDCl$_3$) 7.64(d, 1H), 7.02–6.99(m,2H), 4.04(s,2H), 2.52(s,3H), 2.32(s,3H), 1.38(s,6H).

ii) 4,5-Dihydro-2-[2-[2-[4-methoxy-3-methylphenyl]ethyl]-4-methylphenyl]-4,4-dimethyloxazole n-Butyllithium (14.4 ml, 2.5M solution in hexane) was added dropwise to a stirred solution of the product from step (i) (6.9 g) in THF (100 ml) at 0° C. The solution was stirred at 0° C. for 1 hour and then transferred by cannula into a solution of 4-chloromethyl-1-methoxy-2-methylbenzene (J. Chem. Soc. 1956, 2455) (5.86 g) in THF (60 ml) at –30° C. The mixture was stirred for 1 hour and allowed to warm to room temperature. After 30 minutes the reaction was quenched with water. The mixture was partitioned between ethyl acetate and water. The organic phase was washed with water, dried (MgSO$_4$) and evaporated. Purification was by chromatography eluting with 5% ethyl acetate in isohexane. Yield 2.16 g.

MS: LC-MS: 338 (M+1)

iii) 2-[2-[4-methoxy-3-methylphenyl]ethyl]-4-methylbenzoic acid

Methyl iodide (2 ml) was added to a solution of the product from step (ii) (2.15 g) in acetonitrile (20 ml) and the mixture heated at reflux for 5 hours. The solution was evaporated and the residue treated with a solution of sodium hydroxide (8 g) in water (40 ml) and methanol (50 ml). The mixture was heated at reflux for 6 hours and concentrated under reduced pressure. The aqueous solution was washed with diethyl ether, acidified and extracted with ethyl acetate. The extract was dried (MgSO$_4$) and evaporated. Yield 1.5 g.

MS: APCI(–ve): 283 (M–1)

iv) 10,11-Dihydro-3-methoxy-2,8-dimethyl-5H-dibenzo[a,d]cyclohepten-5-one

The subtitle compound was prepared from the product of step (iii) (1.5 g) according to the method of example 17 step (v). Purification was by chromatography eluting with 5% ethyl acetate in isohexane. Yield 0.5 g.

MS: APCI(+ve): 267 (M+1,100%)

v) (±)-5-[3-Methoxy-2,8-dimethyl-5H-dibenzo[ad(cyclohepten-5-y(]-2,4(1H,3H)-pyrimidinedione The subtitle compound was prepared from the product of step (iv) (0.49 g) according to the method of example 8 step (i). Yield 0.428 g. Used directly in the next step.

vi) (±)-5-[[3,4-Dihydro-5-)3-methoxy-2,8-dimethyl-5H-dibenzo[a,d]cyclohepten-5-yl]-2,4-dioxo-1(2H)-pyrimidinyl]methyl]-2-furancarboxylic acid ethyl ester The subtitle compound was prepared from the product of step (v) (0.42 g) and 5-bromomethyl-2-furancarboxylic acid ethyl ester (J. Chem. Soc. Perkin Trans. 1, 1981, 1125, Bull. Chem. Soc. Jpn. 1987, 60, 1807) (0.466 g) according to the method of example 1 step (iv). Purification was by chromatography eluting with 50% ethyl acetate in isohexane. Yield 0.232 g.

1H NMR: δ (DMSO) 11.24(s,1H), 7.38(d,1H), 7.29(d, 1H), 7.14–7.07(m,4H), 6.68–6.57(m,3H), 6.52(d, 1H), 5.22 (s, 1H), 4.91–4.79(q,2H), 4.34(q,2H), 3.82(s,3H), 2.26(s, 3H), 2.11 (s,3H), 1.33(t,3H).

vii) (±)-5-[[3,4-Dihydro-5-{3-methoxy-2,8-dimethyl-5H-dibenzo[a,d]cyclohepten-5-yl}-2,4-dioxo-1(2H)-pyrimidinyl]methyl]-2-furancarboxylic acid The title compound was prepared from the product of step (vi) (0.095 g) according to the method of example 1 step (vi). Yield 0.018 g.

MS: APCI(+ve): 485 (M+1,100%)

1H NMR: δ (DMSO) 11.23(s,1H), 7.38(d,1H), 7.21(d, 1H), 7.12(d,1H), 7.08–7.07(m,3H), 6.67–6.56(m,3H), 6.49 (d,1H), 5.22(s,1H), 4.90.4.76(q,2H), 3.82(s,3H), 2.26(s,3H), 2.11(s,3H).

MP: 170° C.

EXAMPLE 22

(±)-5-[[3,4-Dihydro-5-{1,2,8-trimethyl-5H-dibenzo[a,d]cyclohepten-5-yl}-2-oxo-4-thioxo-1(2H)-pyrimidinyl]methyl]-2-furancarboxylic acid i) 1-Bromomethyl-2,3-dimethylbenzene A mixture of 1-hydroxymethyl-2,3-dimethylbenzene (ref) (5 g) and phosphorous tribromide (1.16 ml) in benzene (50 ml) was heated at reflux for 3 hours. The mixture was diluted with toluene, washed with water, dried (MgSO$_4$) and evaporated. Yield 7 g.

MS: GC-MS: 200/198 (M)

ii) 4,5-Dihydro-4,4-dimethyl-2-[4-methyl-2-[2-[2,3-dimethylphenyl]ethyl]phenyl]oxazole n-Butyllithium (6.9 ml of a 2.5M soln in hexanes) was added dropwise to the product of example 21 step (i) (3.51 g) in tetrahydrofuran (60 ml) at –78° C. After 2 hours the product from step (i) (3.45 g) was added. After 1 hour the solution was left to warm to room temperature. The solution was quenched with water and extracted with ethyl acetate. The organic solution was dried (MgSO$_4$) and evaporated under reduced pressure. Yield 1.83 g.

MS: APCI(+ve): 322 (M+1, 100%)

iii) 2-[2-[2,3-Dimethylphenyl]ethyl]-4-methylbenzoic acid

The subtitle compound was prepared from the product of step (ii) (1.83 g) according to the method of example 21 step (iii). Yield 1.32 g.

1H NMR: δ (CDCl$_3$) 7.99(d,1H), 7.13–7.00(m,5H), 3.26–3.21(m,2H), 3.02–2.93(m,2H), 2.39(s,3H), 2.29(s,3H), 2.27(s,3H).

iv) 10,11-Dihydro-1,2,8-trimethyl-5H-dibenzo[a,d]cyclohepten-5-one

The subtitle compound was prepared from the product of step (iii) (1.32 g) according to the method of example 17 step (v). Purification was by chromatography eluting with toluene. Yield 0.86 g.

1H NMR: δ (CDCl$_3$) 7.80–7.77(d,1H), 7.65–7.62(d,1H), 7.12(brs,1H), 7.09(brs,1H), 7.01(brs,1H), 3.15(s,4H), 2.36 (s,3H), 2.34(s,3H), 2.25(s,3H).

v) (±)-5-[1,2,8-Trimethyl-5H-dibenzo[a,d]cyclohepten-5-yl]-2,4(1H,3H)-pyrimidinedione The subtitle compound was prepared from the product of step (iv) (0.85 g) according to the method of example 8 step (i). Yield 0.95 g. Product used directly in the next step.

vi) (±)-5-[[3,4-Dihydro-5-{1,2,8-trimethyl-5H-dibenzo[a,d]cyclohepten-5-yl}-2,4-dioxo-1(2H)-pyrimidinyl]methyl]-2-furancarboxylic acid, ethyl ester The subtitle compound was prepared from the product of step (v) (0.95 g) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.64 g) according to the method of example 1 step (iv). Purification was by chromatography eluting with 20% ethyl acetate in toluene. Yield 1.02 g.

MS: APCI(+ve): 497 (M+1, 100%)

vii) (±)-5-[[3,4-Dihydro-5-{1,2,8-trimethyl-5H-dibenzo[a,d]cyclohepten-5-yl}-2-oxo-4-thioxo-1(2H)-pyrimidinyl]methyl]-2-furancarboxylic acid, ethyl ester The subtitle compound was prepared from the product of step (vi) (1.02 g) according to the method of example 1 step (v). Purification was by chromatography eluting with 10% ethyl acetate in toluene. Yield 0.62 g.

MS: APCI(+ve): 513 (M+1, 100%)

viii) (±)-5-[[3,4-Dihydro-5-{1,2,8-trimethyl-5H-dibenzo[a,d]cyclohepten-5-yl}-2-oxo-4-thioxo-1(2H)-pyrimidinyl]methyl]-2-furancarboxylic acid The title compound was prepared from the product of step (vii) (0.62 g) according to the method of example 1 step (vi). Yield 0.44 g.

MS: APCI(+ve): 485 (M+l, 100%)

1H NMR: δ (DMSO) 13.26(br s,1H), 12.59(s,1H), 7.42 (d,1H), 7.26–7.23(m,2H), 7.13–6.78(m,6H), 6.61(d,1H), 5.59(br s,1H), 5.00–4.87(m,2H), 2.25(s,3H), 2.22(s,6H).

EXAMPLE 23

5-[[5-{2,8-Bis(trifluoromethyl)-5H-dibenzo[a,d]cyclohepten-5-yl}-3,4-dihydro-2-oxo-4-thioxo-1(2H)-pyrimidinyl]methyl]-2-furancarboxylic acid i) 4,5-Dihydro-4,4-dimethyl-2-[4-trifluoromethylphenyl]oxazole To a solution of 2-amino-2-methyl-1-propanol (21.4 g) in dichloromethane (100 ml) at 0C was added dropwise a solution of 4-(trifluoromethyl)benzoyl chloride (25 g). The mixture was stirred at room temperature for 16 hours, washed with 2M HCl then sodium bicarbonate solution, dried (MgSO$_4$) and evaporated. The residue was dissolved in dichloromethane (100 ml) and treated with thionyl chloride (14 ml) at 0C. The mixture was stirred at room temperature for 2 hours and evaporated. The residue was partitioned between ethyl acetate and aqueous potassium hydroxide. The organic phase was dried (MgSO$_4$) and evaporated. Yield 14.57 g.

1H NMR: δ (CDCl$_3$) 8.05(d,2H), 7.67(d,2H), 4.14(s,2H), 1.40(s,6H).

ii) 4,5-Dihydro-4,4-dimethyl-2-[2-methyl-4-[trifluoromethyl]phenyl]oxazole

To a solution of the product from step (i) (9.5 g) in tetrahydrofuran (40ml) at −60° C. was added n-butyllithium (17 ml of a 2.5M solution in hexanes) dropwise. The mixture was stirred at −65° C. for 1 hour and methyl iodide (12 ml) was added. The mixture was stirred at room temperature for 1 hour and quenched with brine. The organic phase was dried (MgSO$_4$) and evaporated. Yield 9.56 g. Used directly in the next step.

iii) 2-[2-[2-[3-Bromophenyl]ethyl]-4-[trifluoromethyl]phenyl]-4,5-Dihydro-4,4-dimethyloxazole n-Butyllithium (1.6 ml of a 2.5M solution in hexanes) was added to the product of step (ii) (0.59 g) in tetrahydrofuran (15 ml) at −65° C. After 1.5 hours 3-bromobenzyl bromide (1.0 g) in tetrahydrofuran (6 ml) was added. The reaction was stirred at room temperature for 2 hours, partitioned between brine and ethyl acetate, dried (MgSO$_4$) and evaporated under reduced pressure. Purification was by chromatography eluting with 10% ethyl acetate in isohexane. Yield 0.44 g.

MS: APCI(+ve): 426/8 (M+1, 100%)

iv) 2-[2-[3-Bromophenyl]ethyl]-4-[trifluoromethyl]benzoic acid

The subtitle compound was prepared from the product of step (iii) (4.2 g) according to the method of example 21 step (iii). Yield 2.41 g.

MS: APCI(−ve): 371/3 (M−1, 100%)

v) 2-Bromo-10,11-dihydro-8-[trifluoromethyl]-5H-dibenzo[a,d]cyclohepten-5-one

A mixture of the product from step (iv) (2.31 g) and phosphorous pentoxide (14 g) in nitrobenzene (15 ml) was heated at 100° C. for 8 hours. The solid mixture was added to water, salted out and extracted with ethyl acetate. The extract was dried (MgSO$_4$) and evaporated, distilled to remove nitrobenzene and the residue purified by chromatography eluting with 10% ethyl acetate in isohexane. Yield 1.14 g.

MS: GC-MS: 354/6 (M$^+$)

vi) 2,8-Bis[trifluoromethyl-10,11-dihydro-5H-dibenzo[a,d]cyclohepten-5-one

A mixture of the product from step (v) (1.14 g), sodium trifluoroacetate (3.52 g) and copper (1) iodide (2.35 g) in dimethylformamide (30ml) was heated at 160° C. for 19 hours. The mixture was evaporated and the residue partitioned between ethyl acetate and water. The organic phase was dried (MgSO$_4$), evaporated and purified by chromatography eluting with is 5% ethyl acetate in isohexane. Yield 0.71 g.

1H NMR: δ (CDCl$_3$) 8.09(d,2H), 7.60(d,2H), 7.53(s,2H), 3.31(s,4H).

vii) 5-[2,8-Bis(trifluoromethyl)-5H-dibenzo[a,d]cyclohepten-5-yl]-2,4(1H,3H)-pyrimidinedione The subtitle compound was prepared from the product of step (vi) (0.71 g) according to the method of example 8 step (i) followed by heating the residue in trifluoroacetic acid at reflux. The solvent was evaporated to give a solid. Used directly in the next step.

viii) 5-[[5-{2,8-Bis[trifuoromethyl]-5H-dibenzo[a,d]cyclohepten-5-yl}-3,4-dihydro-2,4-dioxo-1(2H)-pyrimidinyl]methyl]-2-furancarboxylic acid, ethyl ester The subtitle compound was prepared from the product of step (vii) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.73 g) by the method of example 1 step (iv). Purification was by chromatography eluting with 40% ethyl acetate in isohexane. Yield 0.43 g.

1H NMR: δ (CDCl$_3$) 8.68(s,2H), 7.70–7.60(m,6H ), 7.15 (d,2H), 7.06(s,2H ), 6.70(s,1H), 6.44(d,1H), 5.47(s,1H), 4.76(s,2H), 4.45(q,2H), 1.45(t,3H).

ix) 5-[[5-{2,8-Bis[trifluoromethyl]-5H-dibenzo[a,d]cyclohepten-5-yl}-3,4-dihydro-2-oxo-4-thioxo-1(2H)-pyrimidinyl]methyl]-2-furancarboxylic acid, ethyl ester The subtitle compound was prepared from the product of step (viii) (0.25 g) according to the method of example 1 step (v). Yield 0.11 g.

MS: APCI(−ve): 605 (M−1)

x) 5-[[5-{2,8-Bis[trifluoromethyl]-5H-dibenzo[a,d]cyclohepten-5-yl}-3,4-dihydro-2-oxo-4-thioxo-1(2H)-pyrimidinyl]methyl]-2-furancarboxylic acid The title compound was prepared from the product of step (ix) (0.11 g) according to the method of example 1 step (vi). Yield 0.074 g.

MS: APCI(−ve): 577 (M−1)

1H NMR: δ (DMSO) 12.74(s,1H), 7.91(d,2H), 7.76(m, 4H), 7.20(d,1H), 7.14(s,2H), 6.98(br s,1H), 6.58(d,1H), 6.00 (s,1H), 4.97(s,2H).

MP: 159–162° C.

EXAMPLE 24

5-[[5-{2,8-Bis[trifluoromethyl]-5H-dibenzo[a,d]cyclohepten-5-yl}-3,4-dihydro-2,4-dioxo-1(2H)-pyrimidinyl]methyl]-2-furancarboxylic acid The title compound was prepared from the product of example 23 step (viii) (0.12 g) according to the method of example 1 step (vi). Yield 0.05 g.

MS: APCI(−ve): 561 (M−1)

1H NMR: δ (DMSO) 7.83(d,2H), 7.74(d,4H), 7.13(s,2H), 6.94(s,1H), 6.67(s,1H), 637(d,1H), 5.60(s,1H), 4.83(s,2H).

MP: 203–206° C.

EXAMPLE 25

(±)-5-[[5-{2-Ethyl-8-methyl-5H-dibenzo[a,d]cyclohepten-5-yl}-3,4-dihydro-2,4-dioxo-1(2H)-pyrimidinyl]methyl]-2-furancarboxylic acid i) 3-Ethylbenzenemethanol n-Butyllithium (34 ml of a 2.5M solution in hexanes) was added to a solution of 1-bromo-3-ethylbenzene (15 g) in tetrahydrofuran at −78° C. After 1 hour dimethylformamide (15 ml) was added. The mixture was stirred at −78° C. for 1 hour and allowed to warm to room temperature. The mixture was quenched with aqueous ammonium chloride and partitioned between ethyl acetate and water. The organic phase was dried (MgSO$_4$) and evaporated. The residue was dissolved in methanol (250 ml) and treated with sodium borohydride (1.51 g) portionwise. The mixture was stirred at room temperature for 16 hours, quenched with 2M HCl (100 ml) and stirred for 4 hours. The mixture was concentrated under reduced pressure and the residue partitioned between ethyl acetate and 2M HCl. The organic phase was dried (MgSO$_4$), evaporated and the residue purified by chromatography eluting with 5–10% ethyl acetate in isohexane. Yield 7.6 g.

MS: GC-MS: 136 (M$^+$)

ii) 1-Bromomethyl-3-ethylbenzene Phosphorous tribromide (5.3 ml) was added to a solution of the product from step (i) (7.6 g) in benzene (150 ml) at 0° C. After 3 hours water (40 ml) was added and the mixture warmed to room temperature and extracted with ethyl acetate. The organic phase was dried (MgSO$_4$) and evaporated. Purified by chromatography eluting with 2% ethyl acetate in isohexane. Yield 8.0 g.

1H NMR: δ (CDCl$_3$) 7.28–7.12(m,4H), 4.48(s,2H), 2.65 (q,2H), 1.24(t,3H).

iii) 2-[2-[2-[3-Ethylphenyl]ethyl]-4-methylphenyl]-4,5-dihydro-4,4-dimethyloxazole The subtitle compound was prepared from the product of step (ii) (8.0 g) and the product from example 21 step (i) (8.13 g) according to the method of example 21 step (ii). Purification was by chromatography eluting with 5% ethyl acetate inisohexane. Yield 4.93 g.

MS: APCI(+ve): 322 (M+1, 100%)

iv) 2-[2-[3-Ethylphenyl]ethyl]-4-methylbenzoic acid

The subtitle compound was prepared from the product of step (iii) (4.9 g) according to the method of example 21 step (iii). Used directly in the next step.

v) 2-Ethyl-10,11-dihydro-8-methyl-5H-dibenzo[a,d]cyclohepten-5-one

A mixture of the product from step (iv) in polyphosphoric acid (40 g) and sulpholane (20 ml) was heated at 130° C. for 5 hours and partitioned between ethyl acetate and water. The organic phase was washed with aqueous sodium bicarbonate and water, dried (MgSO$_4$) and evaporated. Purified by chromatography eluting with 5% ethyl acetate inisohexane.

MS: GC-MS: 250 (M$^+$)

vi) (±)-5-[2-Ethyl-8-methyl-5H-dibenzo[a,d]cyclohepten-5-yl]-2,4(1H,3H)-pyrimidinedione The subtitle compound was prepared from the product of step (v) (3 g) according to the method of example 8 step (i). Yield 1.48 g.

MS: LC-MS: APCI(+ve): 345 (M+1, 100%)

vii) (±)-5-[[5-{2-Ethyl-8-methyl-5H-dibenzo[a,d]cyclohepten-5-yl}-3,4-dihydro-2,4-dioxo-1(2H)-pyrimidinyl]methyl]-2-furancarboxylic acid, ethyl ester The subtitle compound was prepared from the product of step (vi) (0.6 g) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.47 g) according to the method of example 1 step (iv). Purification was by chromatography eluting with 50% ethyl acetate in isohexane. Yield 0.19 g.

1H NMR: δ (DMSO) 11.24(s,1H), 7.39(m,2H), 7.29(d, 1H), 7.20–7.12(m,4H), 6.74(s,2H), 6.62(s,1H), 6.52(d,1H), 5.22(s,1H), 4.86(s,2H), 4.34(q,2H), 2.57(q,2H), 2.27(s,3H), 1.34(t,3H), 1.18(t,3H).

viii) (±)-5-[[5-{2-Ethyl-8-methyl-5H-dibenzo[a,d]cyclohepten-5-yl}-3,4-dihydro-2,4-dioxo-1(2H)-pyrimidinyl]methyl]-2-furancarboxylic acid The title compound was prepared from the product of step (vii) (0.18 g) according to the method of example 1 step (vi). Yield 0.06 g.

1H NMR: δ (DMSO) 11.24(s,1H), 7.41–7.11(m,7H), 6.74 (s,2H), 6.61(s,1H), 6.49(d,1H), 5.21(s,1H), 4.84(s,2H), 2.57 (q,2H), 2.27(s,3H), 1.15(t,3H).

MS: APCI(+ve): 469 (M+1, 100%)

MP: 253° C.

EXAMPLE 26

(±)-5-[[5-{2-Ethyl-5H-dibenzo[a,d]cyclohepten-5-yl}-3,4-dihydro-2,4-dioxo-1(2H)-pyrimidinyl]methyl]-2-furancarboxylic acid i) 4,5-Dihydro-4,4-dimethyl-2-[2-methylphenyl]oxazole The subtitle compound was prepared from o-toluoyl chloride (25 g) according to the method of example 23 step (i). Yield 24.1 g. Used directly in the next step.

ii) 2-[2-[2-[3-Bromophenyl]ethyl]phenyl]-4,5-dihydro-4,4-dimethyloxazole

The subtitle compound was prepared from the product of step (i) (1 g) and 3-bromobenzylbromide (1.32 g) according to the method of example 21 step (ii). Purification was by chromatography eluting with 5–10% ethyl acetate inisohexane. Yield 0.64 g.

1H NMR: δ (CDCl$_3$) 7.80(d,1H), 7.45(s,1H), 7.40–7.30 (m,2H), 7.30–7.20(m,2H), 7.13(d,2H), 4.10(s,2H), 3.23(m, 2H), 2.88(m,2H), 1.42(s,6H).

iii) 2-[2-[3-Bromophenyl]ethyl]benzoic acid

The subtitle compound was prepared from the product of step (ii) (12.4 g) according to the method of example 21 step (iii).Yield 9.3 g.

MS: APCI(−ve): 303/5 (M−1)

iv) 2-Bromo-10,11-dihydro-5H-dibenzo[a,d]cyclohepten-5-one

The subtitle compound was prepared from the product of step (iii) (9.3 g) according to the method of example 25 step (v). Yield 4.91 g.

MS: GC-MS: 286/8 (M$^+$)

v) 2-Ethyl-10,11-dihydro-5H-dibenzo[a,d]cyclohepten-5-one

A mixture of the product from step (iv) (1.52 g), tetraethyl tin (10.4 ml) and tetrakis(triphenylphosphine)palladium(0) (100 mg) in dimethylformamide (20 ml) was heated at 130° C. for 48 hours. The mixture was evaporated and the residue purified by chromatography eluting with isohexane then 50% toluene in isohexane then toluene. Yield 0.88 g.

1H NMR: δ (CDCl$_3$) 8.00(d+dd,2H), 7.42(t of d,1H), 7.34(td,1H), 7.22(d,1H), 7.17(dd,1H), 7.05(s,1H), 3.19(s, 4H), 2.67(q,2H), 1.31(s,3H), 1.26(t,3H).

vi) (±)-5-[2-Ethyl-5H-dibenzo[a,d]cyclohepten-5-yl]-2,4 (1H,3H -pyrimidinedione

The subtitle compound was prepared from the product of step (v) (0.88 g) according to the method of example 8 step (i). Yield 1.16 g. Used directly in the next step.

vii) (±)-5-[[5-{2-Ethyl-5H-dibenzo[a,d]cyclohepten-5-yl}-3,4-dihydro-2,4-dioxo-1(2))-pyrimidinyl]methyl]-2-furancarboxylic acid, ethyl ester The subtitle compound was prepared from the product of step (vi) (1.16 g) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.91 g) according to the method of example 1 step (iv). Purification was by chromatography eluting with 30% ethyl acetate in toluene. Yield 0.47 g.

1H NMR: δ (CDCl$_3$) 8.23(br s,1H), 7.49(d,1H), 7.42(d, 1H), 7.38–7.25(m,3H), 7.20(dd,2H), 7.15(d,2H), 6.83(s, 2H), 6.70(s, 1H), 6.40(d, 1H), 5.31 (s, 1H), 4.74(s,2H), 4.44(q,2H), 2.63(q,2H), 1.45(t,3H), 1.22(t,3H).

viii) (±)-5-[[5-{2-Ethyl-5H-dibenzo[a,d]cyclohepten-5-yl}-3,4-dihydro-2,4-dioxo-1(2H)-pyrimidinyl]methyl]-2-furancarboxylic acid The title compound was prepared from the product of step (vii) (0.15 g) according to the method of example 1 step (vi). Yield 0.085 g.

MS: APCI(+ve): 455 (M+1, 100%)

1H NMR: δ (DMSO) 7.49(d,1H), 7.41(d,1H), 7.36–7.10 (m,5H), 6.99(d,1H), 6.80(s,2H), 6.62(s,1H), 6.40(d,1H), 5.26(s,1H), 4.80(s,2H), 2.55(q,2H), 1. 14(t,3H).

MP: 178–180° C.

EXAMPLE 27

N-[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]-L-aspartic acid i) N-[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]-L-aspartic acid, dimethyl ester The subtitle compound was prepared from example 11(0.92 g) and L-aspartic acid dimethyl ester according to the method of example 15 step (i) with the addition of 4-dimethylaminopyridine (0.24 g). Purification was by chromatography eluting with 1–3% methanol in dichloromethane. Yield 0.97 g.

MS: APCI(+ve): 614 (M+1, 100%)

ii) N-[5-[[5-{2,8-Dimethyl-5H-dibenzo[a,d]cyclohepten-5-yl}-3,4-dihydro-2-oxo-4-thioxo-1(2H)-pyrimidinyl]methyl] furan-2-ylcarbonyl]-L-aspartic acid The title compound was prepared from the product of step (i) (0.96 g) according to the method of example 1 step (vi). Yield 0.45 g.

MS: APCI(+ve): 586 (M+1, 100%)

1H NMR: δ (DMSO) 12.70(br s,1H), 12.62(s,1H), 8.65 (d,1H), 7.42(dd,2H), 7.22(d,1H), 7.14(s,1H), 7.10(br s,3H), 6.82(s,1H), 6.69–6.61(m,2H), 6.56(d,1H), 5.70(s,1H), 4.88 (s,2H), 4.79(br q,1H), 2.93–2.71(m,2H), 2.27(s,6H).

MP: 195° C.

EXAMPLE 28

2-[[5-{10,11-Dihydro-5H-dibenzo[a,d]cyclohepten-5-yl}-3, 4-dihydro-2-oxo-4-thioxo-1(2H)-pyrimidinyl]methyl]-4-thiazolecarboxylic acid i) 5-[10,11-Dihydro-5H-dibenzo[a,d]cyclohepten-5-yl]-2,4 (1H,3H)-pyrimidinedione The subtitle compound was prepared from 5-bromo-2,4-bis(1,1-dimethylethoxy)pyrimidine (example step(i)) (3.5 g) and 10,11-dihydro-5H-dibenzo[a,d]cyclohepten-5-one (2.41 g) according to the method of example 1 step (iii). Purification was by chromatography eluting with 2% ethanol in dichloromethane. Yield 2.17 g. Used directly in the next step.

ii) 2-[[5-{10,11-Dihydro-5H-dibenzo[a,d]cyclohepten-5-yl}-3,4-dihydro-2,4-dioxo-1(2H)-pyrimidinyl]methyl]-4-thiazolecarboxylic acid, ethyl ester The subtitle compound was prepared from the product of step (i) (1.37 g) according to the method of example 1 step (iv). Purification was by chromatography eluting with 1% ethanol in dichloromethane. Yield 1.3 g 1H NMR: δ(DMSO) 11.48(s, 1H), 8.5 (s, 1H), 7.32(d, 2H), 7.13(m, 6H), 7.02(s, 1H), 5.22(d, 2H), 5.1(s, 1H), 4.32(q, 2H), 3.38(m, 2H), 2.72(m, 2H), 1.32(t, 3H).

iii) 2-[[5-{10,11-Dihydro-5H-dibenzo[a,d]cyclohepten-5-yl}-3,4-dihydro-2-oxo-4-thioxo-1(2H)-pyrimidinyl]methyl]-4-thiazolecarboxylic acid, ethyl ester The subtitle compound was prepared from the product of step (ii) (1.3 g) according to the method of example 1 step (v). Purification was by chromatography eluting with 0.5% ethanol and 50% dichloromethane in isohexane. Yield 0.75 g.

1H NMR: δ(DMSO) 12.86 (s, 1H), 8.53(s, 1H), 7.36(d, 2H), 7.06–7.38(m, 7H), 5.56(s, 1H), 5.3(s, 2H), 4.33(q, 2H), 3.37(m, 2H), 2.73(m, 2H), 1.33(t, 3H).

iv) 2-[[5-{10,11-Dihydro-5H-dibenzo[a,d]cyclohepten-5-yl}-3,4-dihydro-2-oxo-4-thioxo-1(2H)-pyrimidinyl]methyl]-4-thiazolecarboxylic acid The title compound was prepared from the product of step (iii) (0.65 g) according to the method of example 1 step (vi). Yield 0.28 g.

MS: APCI(+ve): 462 (M+1, 100%)

1H NMR: δ(DMSO) 13.12 (br s, 1H), 12.86(s, 1H), 8.44(s, 1H), 7.37(d, 2H), 7.22(s, 1H), 7.05–7.16(m, 6H), 5.57(s, 1H), 5.29(s, 2H), 3.4(m, 2H+H2O), 2.73(m, 2H).

EXAMPLE 29

(±)-5-[[3,4-Dihydro-5-{2-methyl-8-[1-methylethyl]-5H-dibenzo[a,d]cyclohepten-5-yl}-2,4-dioxo-1(2H)-pyrimidinyl]methyl]-2-furancarboxylic acid i) 4,5-Dihydro4,4-dimethyl-2-[4-[1-methylethyl]phenyl]oxazole The subtitle compound was prepared from 4-[1-methylethyl]benzoic acid (25.3 g) according to the method of example 21 step (i). Yield 26.13 g.

MS: APCI(+ve): 218(M+1, 100%)

ii) 4,5-Dihydro-4,4-dimethyl-2-[2-methyl-4-[1-methylethyl]phenyl]oxazole n-Butyllithium (52.8 ml of a 2.5M solution in hexanes) was added dropwise to a stirred solution of the product of step (i) (27.6 g) in tetrahydrofuran (100 ml)at –20° C. After 2 hours methyl iodide (85.3 g) was added and the mixture was stirred for 2 hours at this temperature then 0.5 hours at room temperature. The reaction mixture was partitioned between brine and ethyl acetate. The aqueous solution was extracted with ethyl acetate. The organic solution was dried (MgSO$_4$) and evaporated under reduced pressure. Purification was by chromatography eluting with 5% ethyl acetate inisohexane. Used without further purification.

iii) 4,5-Dihydro-4,4-dimethyl-2-[4-[1-methylethyl]-2-[2-[3-methylphenyl]ethyl]phenyl]oxazole The subtitle compound was made from the product of step (ii) and 3-bromomethyltoluene (9.25 g) according to the method of example 21 step (ii). Purification was by chromatography eluting with toluene. Yield 4.8 g.

MS: APCI(+ve): 336(M+1, 100%)

iv) 4-[1-Methylethyl]-2-[2-[3-methylphenyl]ethyl]benzoic acid

The subtitle compound was made from the product of step (iii) (4.85 g) according to the method of example 21 step (iii). Yield 3.43 g.

MS: APCI(–ve): 281 (M–1, 100%)

v) 10,11-Dihydro-2-methyl-8-[1-methylethyl]-5H-dibenzo[a,d]cyclohepten-5-one

The subtitle compound was prepare from the product of step (iv) (3.36 g) according to the method of example 17 step (v) except the reaction was heated at 120° C. for 4 hours. Yield 2.73 g.

MS: APCI(+ve): 265 (M+l, 100%)

vi) (±)-5-[2-Methyl-8-[1-methylethyl]-5H-dibenzo[a,d]cyclohepten-5-yl]-2,4(1H,3H)-pyrimidinedione The subtitle compound was prepared from the product of step (v) (2.73 g) according to the method of example 8 step (i). Yield 2.8 g. Used directly.

vii) (±)-5-[[3,4-Dihydro-5-{2-methyl-8-[1-methylethyl]-5H-dibenzo[a,d]cyclohepten-5-yl}-2,4-dioxo-1(2H)-pyrimidinyl]methyl]-2-furancarboxylic acid, ethyl ester The subtitle compound was prepared from the product of step (vi) (1 g) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.65 g) according to the method of example 1 step (iv). Purification was by chromatography eluting with 20% ethyl acetate in toluene. Yield 0.375 g.

1H NMR: δ(DMSO) 11.25(s, 1H), 7.35–7.43(m, 2H), 7.29(d, 1H), 7.12–7.25(m, 4H), 6.76(s, 2H), 6.63(br s, 1H), 6.52(d, 1H), 5.22(s, 1H), 4.9(d, 1H), 4.82(d, 1H), 4.34(q, 2H), 2.81–2.9(m, 1H), 2.27(s, 3H), 1.34(t, 3H), 1.17(d, 6H).

viii) (±)-5-[[3,4-Dihydro-5-{2-methyl-8-[l(methylethyl]-5H-dibenzo[a,d]cyclohepten-5-yl}-2,4-dioxo-1(2H)-pyrimidinyl]methyl]-2-furancarboxylic acid The title compound was prepared from the product of step (vii) (0.27 g) according to the method of example 1 step (vi). Yield 0. 148 g.

MS: APCI(+ve) 483 (M+1, 100%)

1H NMR: δ(DMSO) 11.24(s, 1H), 7.35–7.42(m, 2H), 7.11–7.25(m, 5H), 6.75(s, 2H), 6.62(s, 1H), 6.49(d, 1H), 5.21(s, 1H), 4.87(d, 1H), 4.80(d, 1H), 2.81–2.90(m, 1H), 2.27(s, 3H), 1.17(d, 6H).

MP: 150–160° C.

EXAMPLE 30

5-[[5-{2,8-Dichloro-5H-dibenzo[a,d]cyclohepten-5-yl}-3,4-dihydro-2-oxo-4-thioxo-1(2H)-pyrimidinyl]methyl]-2-furancarboxylic acid i) 2-[4-Chlorophenyl]-4,5-dihydro-4,4-dimethyloxazole The subtitle compound was prepared from 4-chlorobenzoic acid (10 g) according to the method of example 21 step (i). Yield 11.7 g. Used directly in the next step.

ii) 2-[4-Chloro-2-methylphenyl]-4,5-dihydro-4,4-dimethyloxazole

The subtitle compound was prepared from the product of step (i) (11.7 g) according to the method of example 29 step (ii). Purification was by chromatography eluting with 25–35% ethyl acetate in isohexane. Yield 3.5 g.

1H NMR: δ(CDCl$_3$) 7.69(d, 1H), 7.22(s, 1H), 7.18(dd, 1H), 4.06(s, 2H), 2.54(s, 3H), 1.37(s, 6H).

iii) 2-[4-Chloro-2-[2-[3-chlorophenyl]ethyl]phenyl]-4,5-dihydro-4,4-dimethyloxazole The subtitle compound was made from the product of step (ii) (3.5 g) and 3-chlorobenzyl bromide (2.1 ml) according to the method of example 21 step (ii). Purification was by chromatography eluting with 25% ethyl acetate in isohexane. Yield 2.92 g.

MS: APCI(+ve): 352/350/348 (M+1)

iv) 4-Chloro-2-[2-[3-chlorophenyl]ethyl]benzoic acid

The subtitle compound was made from the product of step (iii) (2.92 g) according to the method of example 21 step (iii). Yield 1.86 g.

MS: APCI(−ve): 293/295/297 (M−1)

v) 2,8-Dichloro-10,11-dihydro-5H-dibenzo[a,d] cyclohepten-5-one

The subtitle compound was prepared from the product of step (iv) (1.76 g) according to the method of example 17 step (v) except the reaction was heated at 150° C. for 5 hours. Purification was by chromatography eluting with 25% ethyl acetate inisohexane. Yield 0.95 g.

MS: GC/MS: 280/278/276(100%)

vi) 5-[2,8-Dichloro-5H-dibenzo[a,d]cyclohepten-5-yl]-2,4 (1H,3H)-pyrimidinedione The subtitle compound was prepared from the product of step (v) (0.87 g) according to the method of example 8 step (i). Yield 0.54 g.

MS: APCI(−ve): 369 (M−1, 100%)

vii) 5-[[5-{2,8-Dichloro-5H-dibenzo[a,d]cyclohepten-5-yl}-3,4-dihydro-2,4-dioxo-1(2H)-pyrimidinyl]methyl]-2-furancarboxylic acid, ethyl ester The subtitle compound was prepared from the product of step (vi) (0.54 g) and 5-bromomethyl-2-furancarboxylic acid ethyl ester (J. Chem. Soc. Perkin Trans. 1, 1981, 1125, Bull. Chem. Soc. Jpn. 1987, 60, 1807)(0.34 g) according to the method of example 1 step (iv). Purification was by chromatography eluting with 30% ethyl acetate in isohexane. Yield 0.55 g.

1H NMR: δ(CDCl$_3$) 8.4(s, 1H), 7.43(d, 2H), 7.3(dd, 4H), 7.13(d, 1H), 6.84(s, 2H), 6.65(s, 1H), 6.43(d, 1H), 5.27(s, 1H), 4.75(s, 2H), 4.44(q,2H), 1.47(t, 3H).

viii) 5-[[5-{2,8-Dichloro-5H-dibenzo[a,d]cyclohepten-5-yl)-3,4-dihydro-2-oxo-4-thioxo-1(2H)-pyrimidinyl] methyl]-2-furancarboxylic acid, ethyl ester The subtitle compound was prepared from the product of step (vii) (0.55 g) according to the method of example 1 step (v). Purification was by chromatography eluting with 30% ethyl acetate in isohexane. Yield 0.27 g.

1H NMR: δ(CDCl$_3$) 9.37(brs, 1H), 7.53(d, 2H), 7.33–7.29(m, 4H), 7.14(d, 1H), 6.89(m, 3H), 6.49(d, 1H), 5.74(s, 1H), 4.78(s, 2H), 4.46(q,2H), 1.45(t, 3H).

ix) 5-[[5-{2,8-Dichloro-5H-dibenzo[a,d]cyclohepten-5-yl}-3,4-dihydro-2-oxo-4-thioxo-1(2H)-pyrimidinyl]methyl]-2-furancarboxylic acid The title compound was prepared from the product of step (vii) (0.27 g) according to the method of example 1 step (vi). Yield 0.13 g.

MS: APCI(−ve): 513/511/509 (M−1) 1H NMR: δ(DMSO) 12.69(s, 1H), 7.64(d, 2H), 7.4 (m, 4H), 7.21(d, 1H), 6.94(s, 1H), 6.90(s, 2H), 6.57(d, 1H), 5.78(s, 1H), 4.95(s, 2H).

EXAMPLE 31

(±)-5-[[5-{2-Ethyl-8-methyl-5H-dibenzo[a,d]cyclohepten-5-yl}-3,4-dihydro-2-oxo-4-thioxo-1(2H)-pyrimidinyl] methyl]-2-furancarboxylic acid i) (±)-5-[[5-{2-Ethyl-8-methyl-5H-dibenzo[a,d] cyclohepten-5-yl}-3,4-dihydro-2-oxo-4-thioxo-1(2H)-pyrimidinyl]methyl]-2-furancarboxylic acid, ethyl ester The subtitle compound was prepared from the product of example 25 step (vii) (0.76 g) according to the method of example 1 step (v). Purification was by chromatography eluting with 10% ethyl acetate in toluene. Yield 0.46 g.

MS: APCI(+ve): 513(M+1)

ii) (±)-5-[[5-{2-Ethyl-8-methyl-5H-dibenzo[a,d] cyclohepten-5-yl}-3,4-dihydro-2-oxo-4-thioxo-1(2H)-pyrimidinyl]methyl]-2-furancarboxylic acid The title compound was prepared from the product of step (i) (0.46 g) according to the method of example 1 step (vi). Yield 0.35 g.

MS: APCI(+ve): 485(M+1)

1H NMR(DMSO) 13.27(br s,1H), 12.64(br s,1H), 7.48(d, 1H), 7.44(d, 1H), 7.24(d, 1H), 7.20–7.10(m, 4H), 6.95(s, 1H), 6.80(dd, 2H), 6.60(d, 1H), 5.74(s, 1H), 4.96(s, 2H), 2.50(q, 2H), 2.27(s, 3H), 1.15(t, 3H)

MP: 165° C.

EXAMPLE 32

(±)-2-[[5-[[5-{2-Ethyl-8-methyl-5H-dibenzo[a,d] cyclohepten-5-yl}-3,4-dihydro-2-oxo-4-thioxo-1(2H)-pyrimidinyl]methyl]furan-2-ylcarbonyl]amino]-4-thiazoleacetic acid i) (±)-2-[[5-[[5-{2-Ethyl-8-methyl-5H-dibenzo[a,d] cyclohepten-5-yl}-3,4-dihydro-2-oxo-4-thioxo-1(2H)-pyrimidinyl]methyl]furan-2-ylcarbonyl]amino]-4-thiazoleacetic acid, ethyl ester The subtitle compound was prepared from the product of example 31(0.2 g) according to the method of example 10 step (i). Purification was by chromatography eluting with 50% ethyl acetate in isohexane. Yield 0.21 g.

MS: APCI(+ve): 653 (M+1)

ii) (+)-2-[[5-[[5-{2-Ethyl-8-methyl-5H-dibenzo[a,d] cyclohepten-5-yl}-3,4-dihydro-2-oxo-4-thioxo-1(2H)-pyrimidinyl]methyl]furan-2-ylcarbonyl]amino]-4-thiazoleacetic acid The title compound was prepared from the product of step (i) (0.21 g) according to the method of example 1 step (vi). Yield 0.056 g.

MS: APCI(+ve): 625 (M+1)

1H NMR: δ (DMSO)12.65(2xbr s, 2H), 12.45(br s,1H), 7.68(d,1H), 7.42(2xd, 2H), 7.20–7.00(m, 5H), 6.95(s, 1H), 6.77(s, 2H), 6.68(d, 1H), 5.76(s, 1H), 4.94(s, 2H), 3.66(s, 2H), 2.50(q, 2H), 2.26(s, 3H), 1.10(t, 3H)

MP: 199° C.

EXAMPLE 33

5-[[5-{2,8-Dimethyl-5H-dibenzo[a,d]cyclohepten-5-yl}-3, 4-dihydro-2-oxo-4-thioxo-1(2H)-pyrimidiny]methyl]-N-[1H-tetrazol-5-yl]-2-furancarboxamide 5 i) 5-[[5-{2,8-Dimethyl-5H-dibenzo[a,d]cyclohepten-5-yl}-3,4-dihydro-2-oxo-4-thioxo-1(2H)-pyrimidiny]methyl]-N-[1H-tetrazol-5-yl]-2-furancarboxamide The title compound was prepared from the product of example 11(0.135 g) according to the method of example 10 step (i) using amino tetrazole (0.036 g). Purification was by chromatography eluting with 10% methanol in dichloromethane. Yield 0.38 g MS: APCI(+ve): 538(M+1, 100%)

1H NMR: δ (DMSO) 12.61(br s, 1H),7.43 (br s, 1H), 7.42(d, 2H), 7.13–7.11(m, 4H), 6.88(s, 1H), 6.73(s, 2H), 6.60(d, 1H), 5.71(s, 1H), 4.90(s, 2H), 2.24(s, 6H).

EXAMPLE 34

(±)-5-[[3,4-Dihydro-5-{2-methyl-8-propyl-5H-dibenzo[a,d] cyclohepten-5-yl}-2-oxo4-thioxo-1(2H)-pyrimidinyl] methyl]-2-furancarboxylic acid i) 1-Bromo-3-propylbenzene A solution of 3-bromopropiophenone (25 g) and triethylsilane (57 ml) in trifluoroacetic acid (50 ml) was heated at reflux for 16 hours. The reaction mixture was evaporated under reduced pressure and the residue was purified by chromatography eluting with isohexane. Yield 25.14 g. The subtitle compound was contaminated with 17 mole % of 3-(1-propenyl)bromobenzene.

1H NMR: δ(CDCl$_3$) 7.32(m,2H), 7.10(m,2H), 2.55(t,2H), 1.61(m,2H), 0.90(t,3H).

ii) 3-Propylbenzenemethanol

The subtitle compound was prepared from the product of step (i) (24.14 g) by the method of example 25 step (i). Used directly in the next step. Yield 15.8 g.

iii) 1-Bromomethyl-3-propylbenzene

The subtitle compound was prepared from the product of step (ii) (15.8 g) by the method of example 25 step (ii). Purification was by chromatography eluting with isohexane. Yield 11.7 g. The subtitle compound was contaminated with 15 mole % of 1-bromomethyl-3-(1-propenyl)benzene.

1H NMR: δ(CDCl$_3$) 7.30–7.10(m,4H), 4.49(d,2H), 2.60 (m,2H), 1.65(m,2H), 0.95(m,3H).

iv) 4,5-Dihydro4,4-dimethyl-2-[4-methyl-2-[2-[3-propylphenyl]ethyl]phenyl]oxazole4

The subtitle compound was prepared from the product of step (iii) (11.7 g) and the product of example 25 step (i) (11.2 g) by the method of example 21 step (ii). Purification was by chromatography eluting with 12% ethyl acetate in isohexane. Yield 15.4 g. The subtitle compound was contaminated with 14 mole % of 4,5-dihydro-4,4-dimethyl-2-[4-methyl-2-[2-[3-[1-propenyl]phenyl]ethyl]phenyl]oxazole.

MS: APCI(+ve): 336 (M+l, 100%).

v) 4-Methyl-2-[2-[3-propylphenyl]ethyl]benzoic acid

The subtitle compound was prepared from the product of step (iv) (15.4 g) by the method of example 21 step (iii). The crude reaction product was contaminated with 4-methyl-2-[2-[3-[1-propenyl]phenyl]ethyl]benzoic acid. The crude reaction product was dissolved in ethyl acetate (100 ml) and the solution was hydrogenated over 10% palladium on carbon (1 g) at 3 atmospheres pressure for 2 hours. The catalyst was removed by filtration and the filtrate was evaporated. Yield 12.8 g.

MS: APCI(-ve): 281 (M-1, 100%).

vi) 10,11-Dihydro-2-methyl-8-propyl-5H-dibenzo[a,d]cyclohepten-5-one.

The subtitle compound was prepared from the product of step (v) (12.8 g) by the method of example 17 step (v). Purification was by chromatography eluting with isohexane. Yield 7.36 g.

MS: APCI(+ve): 265 (M+1, 100%).

vii) (±)-5-[2-Methyl-8-propyl-5H-dibenzo[a,d]cyclohepten-5-yl]-2,4(1H,3H)-pyrimidinedione.

The subtitle compound was prepared from the product of step (vi) (7.0 g) by the method of example 8 step (i). Yield 7.30 g.

MS: APCI(+ve): 359 (M+1).

viii) (±)-5-[[3,4-Dihydro-5-(2-methyl-8-propyl-5H-dibenzo[a,d]cyclohepten-5-yl]-2,4-dioxo-1(2H)-pyrimidinyl]methyl]-2-furancarboxylic acid, ethyl ester The subtitle compound was prepared from the product of step (vii) (2.5 g) by the method of example 1 step (iv). Yield 0.89 g.

MS: APCI(+ve): 511 (M+1,100%)

ix) (±)-5-[[3,4-Dihydro-5-{2-methyl-8-propyl-5H-dibenzo[a,d]cyclohepten-5-yl} 2 oxo-4-thioxo-1(2H)-pyrimidinyl]methyl]-2-furancarboxylic acid, ethyl ester The subtitle compound was prepared from the product of step (viii) (0.89 g) by the method of example 1 step (v). Yield 0.84 g.

MS: APCI(+ve): 527 (M+1)

x) (±)-5-[[3,4-Dihydro-5-{2-methyl-8-propyl-5H-dibenzo[a,d]cyclohepten-5-yl}-2-oxo-4-thioxo-1(2H)-pyrimidinyl]methyl]-2-furancarboxylic acid The title compound was prepared from the product of step (ix) (0.44 g) by the method of example 1 step (vi). Yield 0.37 g.

MS: APCI(+ve): 499 (M+1)

1H NMR: δ (DMSO) 13.26(br s,1H), 12.64(s,1H), 7.45 (t,2H), 7.24(d,1H), 7.16–7.11(m,4H), 6.95(s,1H), 6.76(s, 2H), 6.59(d,1H), 5.74(s,1H), 4.91(s,2H), 2.27(s,3H), 1.56 (sextet,2H).

MP: 188–190° C.

EXAMPLE 35

(±)-2-[[S-[[3,4-Dihydro-5-{2-methyl-8-propyl-5H-dibenzo[a,d]cyclohepten-5-yl}-2-oxo-4-thioxo-1(2H)-pyrimidinyl]methyl]furan-2-yl]carbonyl]amino]-4-thiazoleacetic acid.

i) (±)-2-[[5-[[3,4-Dihydro-5-{2-methyl-8-propyl-5H-dibenzo[a,d]cyclohepten-5-yl}-2-oxo-4-thioxo-1(2H)-pyrimidinyl]methyl]furan-2-yl]carbonyl]amino]-4-thiazoleacetic acid, ethyl ester.

The product of example 34 step (x) (0.32 g), 2-amino-4-thiazoleacetic acid ethyl ester (0.12 g), 4-dimethylaminopyridine (0.12 g) and bromo-tris (pyrrolidino)-phosphonium hexafluorophosphate (0.33 g) were dissolved in dry dimethylformamide (10 ml). N,N-diisopropylethylamine (0.27 ml) was added and the mixture was stirred at room temperature for 72 hours. The reaction mixture was quenched with brine/HCl and extracted with ethyl acetate. The extract was washed with water, dried (MgSO$_4$) and evaporated. The residue was purified by chromatography eluting with 50% ethyl acetate in isohexane. Yield 0.070 g.

MS: APCI(+ve): 667 (M+1)

ii) (±)-2-[[5-[[3,4-Dihydro-5-{2-methyl-8-propyl-5H-dibenzo[a,d]cyclohepten-5-yl}-2-oxo-4-thioxo-1(2H)-pyrimidinyl]methyl]furan-2-yl]carbonyl]amino]-4-thiazoleacetic acid.

The title compound was prepared from the product of step (i) (0.070 g) by the procedure of example 1 step (vi). After the reaction was complete the aqueous solution was washed with ethyl acetate, acidified and extracted with ethyl acetate. The ethyl acetate extracts were dried (MgSO$_4$) and evaporated. Yield (0.048 g).

MS: APCI(+ve): 639 (M+1)

1H NMR: δ (DMSO) 12.65 (brs,1H), 7.67 (d,1H), 7.43 (t,2H), 7.15–7.05 (m,5H), 6.94 (s,1H), 6.73 (q,2H), 6.68 (d,1H), 5.76 (s,1H), 4.93 (q,2H), 3.66 (s,2H), 2.50(2H), 2.22 (s,3H), 1.50 (sextet,2H), 0.82 (t,3H).

MP: 190–193° C.

EXAMPLE 36

5-[[5-{2-ethyl-8-methyl-5H-dibenzo[a,d]cyclohepten-5-yl}-3,4-dihydro-2-oxo-4-thioxo-1(2H)-pyrimidinyl] methyl]-N-[1H-tetrazol-5-yl]-2-furancarboxamide i) 5-[[5-{2-ethyl-8-methyl-5H-dibenzo[a,d]cyclohepten-5-yl]-3,4-dihydro-2-oxo-4-thioxo-1(2H)-pyrimidinyl] methyl]-N-[1H-tetrazol-5-yl]-2-furancarboxamide The title compound was prepared from the product of example 31(0.93 g) and amino tetrazole (0.3 g) according to the method of example 10 step (i). Purification was by precipitation from ethyl acetate-iso-hexane. Yield 0.426 g.

MS: APCI(+ve): 552 (M+1)

1H NMR: δ (DMSO) 12.66(s,1H), 12.22(brs,1H), 7.67(s, 1H), 7.47–7.41(2xd,2H), 7.16–7.09(m,4H), 6.92(s,1H), 6.78–6.70(ABq,2H), 6.69(d,1H), 5.74(s,1H), 4.95(s,2H), 2.52(q,2H), 2.22(s,3H), 1.10(t,3H).

MP: 260° C.

EXAMPLE 37

2-[[5-{2,8-Dimethyl-5H-dibenzo[a,d]cyclohepten-5-yl}-3,4-dihydro-2-oxo-4-thioxo-1(2H)-pyrimidinyl]methyl]-4-oxazolecarboxylic acid (i) 2-[[5-{2,8-Dimethyl-5H-dibenzo[a,d]cyclohepten-5-yl}-3,4-dihydro-2,4-dioxo-1(2H)-pyrimidinyl]methyl)-4-oxazolecarboxylic acid, ethyl ester The subtitle compound was prepared from the product of example 8 step (i) (3.2 g) using the method of example 3 step (i). Purification was by chromatography eluting with 30% ethyl acetate in toluene. Yield 1.85 g.

MS: APCI(+ve): 484 (M+1, 100%)

(ii) 2-[[5-{2,8-Dimethyl-5H-dibenzo[a,d]cyclohepten-5-yl}-3,4-dihydro-2-oxo-4-thioxo-1(2H)-pyrimidinyl]methyl]-4-oxazolecarboxylic acid, ethyl ester The subtitle compound was prepared from the product of step (i) (1.85 g) using the method of example 1 step (v). Purification was by chromatography eluting with 20% ethyl acetate in toluene. Yield 1.05 g.

MS: APCI(+ve): 500 (M+1, 100%)

(iii) 2-[[5-{2,8-Dimethyl-5H-dibenzo[a,d]cyclohepten-5-yl}-3,4-dihydro-2-oxo-4-thioxo-1(2H)-pyrimidinyl]methyl]-4-oxazolecarboxylic acid The title compound was prepared from the product of step (ii) using the method of example 1 step (vi). Yield 0.8 g.

MS: APCI(+ve): 472 (M+1, 100%)

1H NMR: δ (DMSO) 13.21(br s, 1H), 12.73(s, 1H), 8.79(s, 1H), 7.46(d, 2H), 7.1–7.2(m, 4H), 7.07(s, 1H), 6.82(s, 2H), 5.75(s, 1H), 5.08(s, 2H), 2.26(s, 6H).

MP: 273° C.

EXAMPLE 38

2-[[5-{2,8-Dimethyl-5H-dibenzo[a,d]cyclohepten-5-yl}-3,4-dihydro-2-oxo-4-thioxo-1(2H)-pyrimidinyl]methyl]-N-methylsulphonyl-4-oxazolecarboxamide i) 2-[[5-{2,8-Dimethyl-5H-dibenzo[a,d]cyclohepten-5-yl}-3,4-dihydro-2-oxo-4-thioxo-1(2H)-pyrimidinyl]methyl]-N-methylsulphonyl-4-oxazolecarboxamide The product of example 37(0.2 g), bromo-tris (pyrrolidino)-phosphonium hexafluorophosphate (0.38 g), 4-dimethylaminopyridine (0.07 g), methanesulphonamide (0.095 g) and N,N-diisopropylethylamine (0.43 ml) in N,N-dimethylformamide (2 ml) was stirred at room temperature for 16 h. The mixture was partitioned between aqueous tartaric acid and ethyl acetate. The organic solution was dried (MgSO4) and evaporated. Purification was by reverse phase silica gel chromatography (C18-sep-pak) eluting with 50% methanol in 0.1% aqueous ammonium acetate. Yield 0.032 g.

MS: APCI(–ve): 547(M–1, 100%).

1H NMR: δ (DMSO) 12.71(s, 1H), 12.1–12.2(br s, 1H), 8.88(s, 1H), 7.46(d, 2H), 7.1–7.2(m, 4H), 7.08(s, 1H), 6.82(s, 2H), 5.76(s, 1H), 5.11(s, 2H), 3.35(s, 3H), 3.0–3.1 (m, 4H), 2.27(s, 6H), 1.7–1.8(m, 4H).

MP: 145–150° C.

EXAMPLE 39

2-[[5-{2,8-Dimethyl-5H-dibenzo[a,d]cyclohepten-5-yl}-3,4-dihydro-2-oxo-4-thioxo-1(2H)-pyrimidinyl]methyl]-N-methyl-4-oxazolecarboxamide i) 2-[[5-{2,8-Dimethyl-5H-dibenzo[a,d]cyclohepten-5-yl}-3,4-dihydro-2-oxo-4-thioxo-1(2H)-pyrimidinyl]methyl]-N-methyl-4-oxazolecarboxamide N,N'-Carbonyldiimidazole (0.073 g) and the product of example 37(0.2 g) in N,N-dimethylformamide (3 ml) was stirred at room temperature. After 0.5 h Methylamine (0.6 ml of a 2M solution in tetrahydrofuran) was added. After a further 0.5 h the solution was partitioned between water and ethyl acetate. The organic solution was washed with water and brine, dried (MgSO4) and evaporated under reduced pressure. Purification was by chromatography eluting with 20% ethyl acetate in iso-hexane. Yield 0. lg.

MS: APCI(+ve): 485 (M+1, 100%)

1H NMR: δ (DMSO) 12.69(s, 1H), 8.61(s, 1H), 8.14–8.18 (m, 1H), 7.46(d, 2H), 7.16–7.20(m, 4H), 7.04(s, 1H), 6.8(s, 2H), 5.75(s, 1H), 5.32(s, 2H), 3.38(d, 3H), 2.27(s, 6H).

MP: 155–160° C.

Pharmacological Data

The following example describes the assay used to determine how strongly the compounds of the invention bind to P2-purinoceptor 7-TM G-protein coupled receptors. The assay used a human $P2Y_2$ receptor clone which was isolated from HL60 cells cDNA and then stably transfected into a Jurkat cell line (using methods described in "Cloning and Characterisation of a Bovine P2y Receptor" Henderson et al (1995), 212, 2, 648–656; Parr et al Proc. Natl. Acad. Sci USA (1994), 91, 3275–3279 and Proc Natl Acad Sci USA (1994), 91, 13067). The cloned receptor mediates an increase in intracellular calcium in the cell line, which possesses no endogenous nucleotide receptor of its own.

The transfected Jurkat cells were maintained at a concentration of from about $1 \times 10^5$ to $10 \times 10^5$ cells/ml in RPMI containing 4% heat inactivated bovine serum, 2% penicillin/streptomycin and 1% glutamine. The cells were incubated at 37° C. in an atmosphere of air with 5% $CO_2$.

The cells were spun down at 1000 r.p.m. for 5 minutes and resuspended in 10 ml basal salt solution (BSS) containing 125 mM of NaCl, 5 mM of KCl, 1 mM of MgCl, 1.5 mM of $CaCl_2$, 25 mM of HEPES, 5 mM of glucose and 1 mg/ml of bovine serum albumin, having a pH of 7.3. The concentration of cells was determined using a Technicon cell counter.

From $0.75 \times 10^8$ to $1 \times 10^8$ cells were spun down, resuspended to a concentration of $3.3 \times 10^7$ cells/ml in BSS and incubated with either 17 μM fluo-3 AM or 17CM Fura-2 AM at 37° C. for 35 minutes with vigorous shaking. The dye used was dependent upon the fluorescence and absorption properties of the compounds of the invention. In general for compounds of formula (I) wherein $Q^1$ represents a S atom, fluo-3 AM was used and for compounds wherein $Q^1$ represents an O atom, either fluo-3 AM or fura-2 AM were used.

The cells were again spun down and washed once with the same volume of BSS before being resuspended in BSS to a concentration of $1 \times 10^6$ cells/ml ready for testing.

When fluo-3 AM was used as the dye, the cell solution was left at room temperature to recover for approximately 30 minutes before testing.

Fura-2 AM loaded cells were divided into aliquots of about 10 ml and were warmed to 37° C. for 10 minutes before testing.

Calcium responses were measured on a SPEX Fluomax using 508 nm excitation and 525 nm emission wavelengths at room temperature for Fluo-3 AM loaded cells and 340/380 nm excitation and 510 nm emission wavelengths for Fura-2 AM loaded cells. Each cuvette contained 2 ml of cells and was stirred at high speed throughout the test. Basal fluorescence was measured for 5 seconds before 20 μl of a $10^{-2}$–$10^{-6}$M solution of the test compound in water was added to the 2 ml solution of the cells. The response was calibrated by the addition of Triton-X-100(68 μl, 10% solution) and then EGTA (180 μl, 0.5 M solution). For each compound the response was compared to that of UTP.

The compounds exemplified have pA2 values greater than 4.0.

What is claimed is:

1. A compound of formula I or a salt thereof:

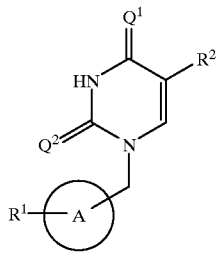
(I)

in which:

A is a 5-membered heterocyclic ring containing 1 to 3 heteroatoms selected from the group consisting of nitrogen, oxygen and sulfur;

$R^1$ is $(CH_2)_nCO_2H$ where n is 1 or 2, $(CH_2)_q$tetrazol-5-yl where q is 0, 1 or 2 or $R^1$ is $COR^3$ where $R^3$ is amino, alkylamino, dialkylamino, NHOalkyl, NHSO$_2$alkyl, OH, $N(CH_2CO_2H)_2$ or a group of formula (i):

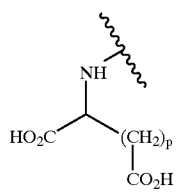
(i)

in which p is 1 or 2, or $R^3$ is a group of formula (ii):

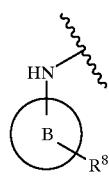
(ii)

where B is a 5-membered heterocyclic ring containing 1 to 4 heteroatoms selected from the group consisting of nitrogen, oxygen and sulfur and $R^8$ is hydrogen or a group $CH_2CO_2H$, $CH_2CON(CH_2CO_2H)_2$ or $CH_2COR^9$ where $R^9$ is a group of formula (i) as defined above or a group of formula (iii):

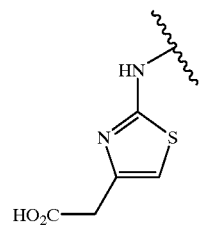
(iii)

$R^2$ is a group of formula (iv) or (v):

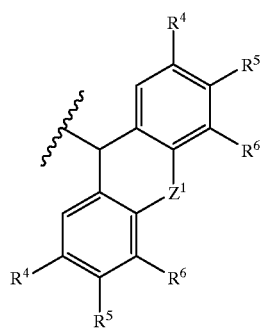
(iv)

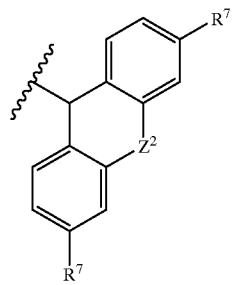
(v)

where $R^4$ groups are independently hydrogen, halogen, methoxy, methylthio or $C_{1-2}$ alkyl (optionally substituted by one or more fluorine atoms);

$R^5$ groups are independently hydrogen, halogen, hydroxy, $C_{1-3}$ alkylthio, $C_{1-4}$ alkyl (optionally substituted by one or more fluorine atoms), $C_{3-4}$ cycloalkyl, MeOCH$_2$, MeSCH$_2$ or $C_{1-2}$ alkoxy;

$R^6$ groups are independently hydrogen, halogen or methyl (optionally substituted by one or more fluorine atoms);

$Z^1$ is CH=CH, CF=CH or CF=CF;

$Z^2$ is a single bond, oxygen, sulphur, CH$_2$CH=CH, CH$_2$CH=CHCH$_2$ or a $C_{1-4}$ alkylene group optionally interrupted by an oxygen or sulphur atom;

$R^7$ is hydrogen, halogen, $C_{1-2}$ alkyl, CF$_3$ or a methylthio group;

$Q^1$ and $Q^2$ each independently represent an O or S;

provided that when $Q^1$ is oxygen, $R^2$ is a group of formula (iv).

2. A compound according to claim 1 in which $R^1$ is a group $COR^3$.

3. A compound according to claim 1 in which $R^3$ is OH, a group of formula (i), $R^3$ is a group of formula (ii) where B is a thiazole and $R^8$ is a group $CH_2CO_2H$ or $CH_2COR^9$ where $R^9$ is a group of formula (i) or $R^3$ is a group of formula (ii) where B is a tetrazole ring and $R^8$ is hydrogen.

4. A compound according to claim 1 in which $R^2$ is a group of formula (iv) where $Z^1$ is CH=CH.

5. A compound according to claim 1 in which $Q^1$ is S and $Q^2$ is O or S.

6. Compounds according to claim 1 which are:

2-[[5-{5H-Dibenzo[a,d]cyclohepten-5-yl}-3,4-dihydro-2-oxo-4-thioxo-1(2H)-pyrimidinyl]methyl]-4-thiazolecarboxylic acid, 2-[[5-{5H-Dibenzo[a,d]cyclohepten-5-yl}-3,4-dihydro-2-oxo-4-thioxo-1(2H)-pyrimidinyl]methyl]-5-thiazolecarboxylic acid, 2-[[5-{5H-Dibenzo[a,d]cyclohepten-5-yl}-3,4-dihydro-2-oxo-4-thioxo-1(2H)-pyrimidinyl]methyl]-4-oxazolecarboxylic acid, 5-[[5-{5H-Dibenzo[a,d]cyclohepten-5-yl}-3,4-dihydro-2-oxo-4-thioxo-1(2H)-pyrimidinyl]methyl]-2-furancarboxylic acid, 5-[5H-Dibenzo[a,d]cyclohepten-5-yl]-3,4-dihydro-1-[4-[1H-tetrazol-5-yl]thiazol-2-ylmethyl]-4-thioxo-2(1H)-pyrimidinone, 4-[5-{5H-Dibenzo[a,d]cyclohepten-5-yl}-3,4-dihydro-2-oxo-4-thioxo-1(2H)-pyrimidinyl]methyl]-2-thiophenecarboxylic acid, 2-[[5-{5H-Dibenzo[a,d]cyclohepten-5-yl}-3,4-dihydro-2-oxo-4-thioxo-1(2H)-pyrimidinyl]methyl]-4-thiazoleacetic acid, 2-[[5-{2,8-Dimethyl-5H-dibenzo[a,d]cyclohepten-5-yl}-3,4-dihydro-2-oxo-4-thioxo-1(2H)-pyrimidinyl]methyl]-4-thiazolecarboxylic acid, N-[2-[[5-{2,8-Dimethyl-5H-dibenzo[a,d]cyclohepten-5-yl}-3,4-dihydro-2-oxo-4-thioxo-1(2H)-pyrimidinyl]methyl]thiazol-4-ylcarbonyl]-L-aspartic acid, 2-[[2-[[5-{2,8-Dimethyl-5H-dibenzo[a,d]cyclohepten-5-yl}-3,4-dihydro-2-oxo-4-thioxo-1(2H)-pyrimidinyl]methyl]thiazol-4-ylcarbonyl]amino]-4-thiazoleacetic acid, 5-[[5-{2,8-Dimethyl-5H-dibenzo[a,d]cyclohepten-5-yl}-3,4-dihydro-2-oxo4-thioxo-1(2H)-pyrimidinyl]methyl]-2-furancarboxylic acid, 5-[[5-{2,8-Dimethyl-5H-dibenzo[a,d]cyclohepten-5-yl}3,4-dihydro-2,4-dioxo-1(2H)-pyrimidinyl]methyl]-2-furancarboxylic acid, 2-[[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonyl]amino]-4-thiazoleacetic acid, 2-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetylamino]-4-thiazoleacetic acid, N-[[2-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]-L-aspartic acid, N-Carboxymethyl-N-[[2-[5-[[5-{2,8-dimethyl-5H-dibenzo[a,d]cyclohepten-5-yl}-3,4-dihydro-2-oxo-4-thioxo-1(2H)-pyrimidinyl]methyl]furan-2-ylcarbonylamino]thiazol-4-yl]acetyl]glycine, 2-[[5-{2,8-Dibromo-5H-dibenzo[a,d]cyclohepten-5-yl}-3,4-dihydro-2-oxo-4-thioxo-1(2H)-pyrimidinyl]methyl]-4-thiazolecarboxylic acid, (±)-5-[[3,4-Dihydro-5-{2,3,8-trimethyl-5H-dibenzo[a,d]cyclohepten-5-yl}-2-oxo-4-thioxo-1(2H)-pyrimidinyl]methyl]-2-furancarboxylic acid, 2-[[5-{2,8-Diethyl-5H-dibenzo[a,d]cyclohepten-5-yl}-3,4-dihydro-2-oxo-4-thioxo-1(2H)-pyrimidinyl]methyl]-4-thiazolecarboxylic acid, (±)-2-[[3,4-Dihydro-5-{2-methoxymethyl-8-methyl-5H-dibenzo[a,d]cyclohepten-5-yl}-2-oxo4-thioxo-1(2H)-pyrimidinyl]methyl]-4-thiazolecarboxylic acid, (±)-5-[[3,4-Dihydro-5-{3-methoxy-2,8-dimethyl-5H-dibenzo[a,d]cyclohepten-5-yl}-2,4-dioxo-1(2H)-pyrimidinyl]methyl]-2-furancarboxylic acid, (±)-5-[[3,4-Dihydro-5-{1,2,8-trimethyl-5H-dibenzo[a,d]cyclohepten-5-yl}-2-oxo-4-thioxo-1(2H)-pyrimidinyl]methyl]-2-furancarboxylic acid, 5-[[5-{2,8-Bis[trifluoromethyl]-5H-dibenzo[a,d]cyclohepten-5-yl}-3,4-dihydro-2-oxo-4-thioxo-1(2H)-pyrimidinyl]methyl]-2-furancarboxylic acid, 5-[[5-{2,8-Bis[trifluoromethyl]-5H-dibenzo[a,d]cyclohepten-5-yl}-3,4-dihydro-2,4-dioxo-1(2H)-pyrimidinyl]methyl]-2-furancarboxylic acid, (±)-5-[[5-{2-Ethyl-8-methyl-5H-dibenzo[a,d]cyclohepten-5-yl}-3,4-dihydro-2,4-dioxo-1(2H)-pyrimidinyl]methyl]-2-furancarboxylic acid, (±)-5-[[5-{2-Ethyl-5H-dibenzo[a,d]cyclohepten-5-yl}-3,4-dihydro-2,4-dioxo-1(2H)-pyrimidinyl]methyl]-2-furancarboxylic acid, N-[5-[[5-{2,8-Dimethyl-5H-dibenzo[a,d]cyclohepten-5-yl}-3,4-dihydro-2-oxo-4-thioxo-1(2H)-pyrimidinyl]methyl]furan-2-ylcarbonyl]-L-aspartic acid, 2-[[5-{10,11-Dihydro-5H-dibenzo[a,d]cyclohepten-5-yl}-3,4-dihydro-2-oxo-4-thioxo-1(2H)-pyrimidinyl]methyl]-4-thiazolecarboxylic acid, (±)-5-[[3,4-Dihydro-5-{2-methyl-8-[1-methylethyl]-5H-dibenzo[a,d]cyclohepten-5-yl}-2,4-dioxo-1(2H)-pyrimidinyl]methyl]-2-furancarboxylic acid, 5-[[5-{2,8-Dichloro-5H-dibenzo[a,d]cyclohepten-5-yl}-3,4-dihydro-2-oxo-4-thio-1(2H)-pyrimidinyl]methyl]-2-furancarboxylic acid, (±)-5-[[5-{2-Ethyl-8-methyl-5H-dibenzo[a,d]cyclohepten-5-yl}-3,4-dihydro-2-oxo-4-thioxo-1(2H)-pyrimidinyl]methyl]-2-furancarboxylic acid, (±)-2-[[5-[[5-{2-Ethyl-8-methyl-5H-dibenzo[a,d]cyclohepten-5-yl}-3,4-dihydro-2-oxo-4-thioxo-1(2H)-pyrimidinyl]methyl]furan-2-ylcarbonyl]amino]-4-thiazoleacetic acid, 5-[[5-{2,8-Dimethyl-5H-dibenzo[a,d]cyclohepten-5-yl}-3,4-dihydro-2-oxo-4-thioxo-1(2H)-pyrimidiny]methyl]-N-[tetrazol-5-yl]-2-furancarboxamide, 5-[[5-{2,8-Dimethyl-5H-dibenzo[a,d]cyclohepten-5-yl}-3,4-dihydro-2-oxo-4-thioxo-1(2H)-pyrimidiny]methyl]-N-[1H-tetrazol-5-yl]-2-furancarboxamide, (±)-5-[[3,4-Dihydro-5-{2-methyl-8-propyl-5H-dibenzo[a,d]cyclohepten-5-yl}-2-oxo-4-thioxo-1(2H)-pyrimidinyl]methyl]-2-furancarboxylic acid, (±)-2-[[5-[[3,4-Dihydro-5-{2-methyl-8-propyl-5H-dibenzo[a,d]cyclohepten-5-yl}-2-oxo-4-thioxo-1(2H)-pyrimidinyl]methyl]furan-2-yl]carbonyl]amino]-4-thiazoleacetic acid, 5-[[5-{2-ethyl-8-methyl-5H-dibenzo[a,d]cyclohepten-5-yl}-3,4-dihydro-2-oxo-4-thioxo-1(2H)-pyrimidinyl]methyl]-N-[1H-tetrazol-5-yl]-2-furancarboxamide, 2-[[5-{2,8-Dimethyl-5H-dibenzo[a,d]cyclohepten-5-yl}-3,4-dihydro-2-oxo-4-thioxo-1(2H)-pyrimidinyl]methyl]-4-oxazolecarboxylic acid, 2-[[5-{2,8-Dimethyl-5H-dibenzo[a,d]cyclohepten-5-yl}-3,4-dihydro-2-oxo-4-thioxo-1(2H)-pyrimidinyl]methyl]-N-methylsulphonyl-4-oxazolecarboxamide, 2-[[5-{2,8-Dimethyl-5H-dibenzo[a,d]cyclohepten-5-yl}-3,4-dihydro-2-oxo-4-thioxo-1(2H)-pyrimidinyl]methyl]-N-methyl-4-oxazolecarboxamide,
or a salt thereof.

7. A pharmaceutical composition comprising a compound of formula I or a salt or solvate thereof as defined in claim 1 in association with a pharmaceutically acceptable adjuvant, diluent or carrier.

8. A process for the preparation of compounds of formula I which comprises reacting a compound of formula (II):

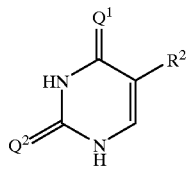

(II)

where $Q^1$, $Q^2$ and $R^2$ are as defined in formula (I) or are protected derivatives thereof with a compound of formula (III):

(III)

where $R^1$ and A are as defined in formula (I) or are protected derivatives thereof and L is a leaving group, and optionally thereafter in any order:
  removing any protecting groups
  converting the compound of formula (I) into a further compound of formula (I)
  forming a salt.

9. A method of treating an inflammatory condition in a patient in need of such treatment, said method comprising the step of administering to said patient a therapeutically effective amount of a compound as claimed in claim 1.

10. A method of treating cancer in a patient in need of such treatment, said method comprising the step of administering to said patient a therapeutically effective amount of a compound as claimed in claim 1.

* * * * *